(12) United States Patent
Schoeniger et al.

(10) Patent No.: US 9,024,111 B1
(45) Date of Patent: May 5, 2015

(54) METHODS AND MATERIALS FOR DECONSTRUCTION OF BIOMASS FOR BIOFUELS PRODUCTION

(75) Inventors: Joseph S. Schoeniger, Oakland, CA (US); Masood Zia Hadi, Castro Valley, CA (US)

(73) Assignee: Sandia Corporation, Albuquerque, NM (US)

( * ) Notice: Subject to any disclaimer, the term of this patent is extended or adjusted under 35 U.S.C. 154(b) by 369 days.

(21) Appl. No.: 13/436,508

(22) Filed: Mar. 30, 2012

Related U.S. Application Data

(60) Provisional application No. 61/469,860, filed on Mar. 31, 2011.

(51) Int. Cl.
| | |
|---|---|
| *C12N 15/82* | (2006.01) |
| *C12N 15/63* | (2006.01) |
| *C12N 15/09* | (2006.01) |
| *A01H 5/04* | (2006.01) |
| *C12N 9/42* | (2006.01) |

(52) U.S. Cl.
CPC .......... *C12N 9/2437* (2013.01); *C12N 15/8255* (2013.01); *C12N 15/8247* (2013.01)

(58) Field of Classification Search
CPC .... C12N 15/82; C12N 9/2402; C12N 9/2437; C12N 15/10; C12N 15/52; C12N 15/63; C12N 15/8221
See application file for complete search history.

(56) References Cited

U.S. PATENT DOCUMENTS

| | | | | |
|---|---|---|---|---|
| 6,391,547 | B1* | 5/2002 | Jefferson et al. | 435/6.13 |
| 2008/0233175 | A1* | 9/2008 | Steer et al. | 424/439 |

OTHER PUBLICATIONS

Genbank Accession No. AJ308623.1, 2005.
Genbank Accession No. AE006641, 2001.
Datta, Supratim, et al., "Ionic Liquid tolerant hyperthermophilic cellulases for biomass pretreatment and hydrolysis", Green Chem., vol. 12, pp. 2338-2345 (2010).
Eckert, K., et al., "Gene cloning, sequencing, and characterization of a family . . . ", Appl. Microbiol Biotechnol, vol. 60, pp. 428-436 (2002).
Hadi, M.Z., et al., "Simple and versatile section of *Arabidopsis* transformants"; Plant Cell Rep., vol. 21, pp. 130-135 (2002).
Hadi, M., "Trojan Horse Strategy for Deconstruction of Biomass for Biofuels Production" presentation slides, presentation slides, presented at the European Conference on Synthetic Biology in Sant Feliu Guixols, Spain, Nov. 23-29, 2007.
Hadi, M., et al., "'Trojan Horse' Strategy for Deconstruction of Biomass for Biofuels Production" poster, presented at the Synthetic Biology 4.0 conference in Hong Kong, Oct. 9-12, 2008.
Hadi, M., "Strategy for Deconstruction of Biomass for Biofuels Production" presentation slides, presented to Innovations in BioFuels 2008 conference in Baltimore, MD, May 13-16, 2008.
Huang, Y., et al., "A highly acid-stable and thermostable endo-B-glucanase from the thermoacidophilic archaeon . . . " Biochem J., vol. 385, pp. 581-588 (2005).
Kim, Seungdo, et al., "Global potential bioethanol production from wasted crops and crop residues"; Biomass and Bioenergy, vol. 26, pp. 361-375 (2004).
Simmons, Bruce., "Green Car Congress"; www.greencarcongress.com/2007/06/sandia_national.html, 2007.
Ziegelhoffer, Thomas., et al., "Dramatic effects of trncation and sub-cellular targeting on the accumulation of recombinjanjt microbial cellulase in tobacco"; Molecular Breeding, vol. 8, pp. 147-158 (2001).

* cited by examiner

*Primary Examiner* — Brent T Page
(74) *Attorney, Agent, or Firm* — Helen S. Baca

(57) ABSTRACT

The present invention relates to nucleic acids, peptides, vectors, cells, and plants useful in the production of biofuels. In certain embodiments, the invention relates to nucleic acid sequences and peptides from extremophile organisms, such as SSO1949 and Ce1A, that are useful for hydrolyzing plant cell wall materials. In further embodiments, the invention relates to modified versions of such sequences that have been optimized for production in one or both of monocot and dicot plants. In other embodiments, the invention provides for targeting peptide production or activity to a certain location within the cell or organism, such as the apoplast. In further embodiments, the invention relates to transformed cells or plants. In additional embodiments, the invention relates to methods of producing biofuel utilizing such nucleic acids, peptides, targeting sequences, vectors, cells, and/or plants.

31 Claims, 13 Drawing Sheets

```
Query = SEQ ID NO: 1 - SSO1949 Wild Type from AE006641 - Length=1005
Subject = SEQ ID NO: 3 - SSO1949 optimized for expression in monocot plants -
Length=1029

Score =  664 bits (736),  Expect = 0.0
 Identities = 707/933 (76%), Gaps = 0/933 (0%)
 Strand=Plus/Plus Query  73    GCTATTTACCTACACCATCAGTCACCTAATGTCAAAACATCATCGATAACTGTCACCACT  132
             ||||| ||| |||| ||||||| ||   ||||||| |||||   || || || || ||
Sbjct  97    GCTATATACTTACATCATCAGAGCCCGAATGTGAAAACGAGCTCAATCACAGTTACAACG  156

Query  133   AACGAAACCACAACTTTAATGAGCATAACAACCAATACCGTACCTACAACAGTAACGCCC  192
             || || || |||||  | |||  |||||| ||||| || || || || || ||| |||
Sbjct  157   AATGAGACTACAACCCTCATGTCAATAACGACCAACACAGTTCCAACTACAGTTACTCCC  216

Query  193   ACTACATCTTCTATTCCTCAGCTAATCTATGTTACATCCTCTGCTAGTTCACCAACTCCA  252
             || |||  |||||| || || ||  || || ||||  || ||| ||   ||| || |||
Sbjct  217   ACCACAAGTTCTATACCACAACTCATTTATGTAACTTCATCTGCCTCTTCGCCCACCCCA  276

Query  253   GTTTATCTAAATAACTCAACTGTACCATCATTTTATCTTGAAGTGAACATGTGGAATGCT  312
             || |||  |||| ||    ||||| ||    |||||   || |||| |||||||||||||
Sbjct  277   GTCTATTTAAACAATAGCACTGTCCCAAGCTTCTATTTAGAAGTAAATATGTGGAATGCA  336

Query  313   AAAACTTGGAATGGCAACTATACCATGGTCTTTAACCCGCTTACTCGTACGCTCTCTGTT  372
             ||||| ||||| || ||  ||||  |||||  |||||| |||| || || |||  |
Sbjct  337   AAAACCTGGAACGGCAATTACACTATGGTTTTTAATCCGCTAACTCGTACTTTAAGCGTC  396

Query  373   AGTTTCAACTTAACGCAAGTTAATCCATTACAGTGGACTAATGGCTATCCGGAAATTTAC  432
              | | ||||||| ||| |||| |||||| | || ||||||| |||||||| ||||||||
Sbjct  397   TCCTTTAACTTAACACAAGTCAATCCTCTTCAATCGACTAACGGCTATCCTGAAATTTAC  456

Query  433   GTGGGCAGAAAACCCTGGGATACTTCATATGCAGGTAACATATTCCCAATGAGGATAGGC  492
             ||||||||  | || ||||| || || |||||||||| ||||| ||||||| ||  ||
Sbjct  457   GTGGGCAGGAAGCCATGGGACACGTCATATGCAGGCAATATTTTCCCCATGCGCATTGGT  516

Query  493   AATATGACACCGTTTATGGTATCGTTTACATAAACTTAACTAAGCTAGACCCGTCAATA  552
             ||||||| | |||| |||||| ||| || ||||| | || ||    ||||  ||    ||
Sbjct  517   AATATGACTCCGTTCATGGTGTCATTCACATAAATCTCACAAAATTAGATCCTAGCATC  576

Query  553   AATTTCGATATTGCGTCTGACGCTTGGATAGTTAGGCCTCAAATAGCATTTAGTCCCGGA  612
             ||||| || ||||| |||||||| |||||||||||  ||||  |||||||||||| || ||
Sbjct  577   AATTTTGACATTGCATCAGATGCATGGATAGTAAGACCGCAGATAGCTTTCAGTCCAGGG  636

Query  613   ACTGCTCCAGGTAATGGGACATTGAGATAATGGTCTGGTTATTAGTCAGAATTTACAG  672
             |||| || ||| || |||| ||||| || |||||| ||      |||||  ||||
Sbjct  637   ACTGCGCCTGGAAATGGTGATATTGAAATAATGGTTTGGTTGTTCTCACAGAACCTACAA  696

Query  673   CCTGCTGGGCAACAAGTTGGAGAAGTAGTAATCCCAATATATATTAATCACACTCTAGTC  732
             || ||||| || ||||| ||||||||| || || || |||||  | || |||| ||||||
Sbjct  697   CCAGCTGGCCAGCAAGTCGGCGAAGTAGTCATACCAATTTACATAAATCATACTTTAGTC  756
```

FIG. 2

```
Query  733   AACGCCACTTTCCAAGTGTGGAAGATGAAGAACGTCCCATGGGGAGGTTGGGAGTACATA  792
```

```
               !!!!! !! !!!!! !! !!!!!!!!!!!!!!!! !! !!!!! !! !!!!!!!!!!!
Sbjct   757   AACGCTACATTCCAGGTTTGGAAGATGAAGAACGTACCCTGGGGTGGATGGGAGTACATC   816

Query   793   GCATTTAGACCAGATGGCTGGAAAGTCACAAATGGTTACGTCGCATATGAGCCCAACTTG   852
               !! !! !! !! !! !! !!!!!!!! !! !!!!! !! !!!!! !!!!!!!! !!! !
Sbjct   817   GCTTTCAGGCCTGACGGTTGGAAAGTAACTAATGGATATGTCGCGTATGAGCCAAACCTA   876

Query   853   TTCATCAAAGCGTTAAATAATTTCGCAAGCTACAACATTACAAACTATTACTTAACGGAT   912
               !! !! !!!!! !!!!!!!! !!!!!!    !! !!!!! !! !!!!! !!   !!! !!!
Sbjct   877   TTTATAAAAGCCTTAAATAACTTCGCATCTTATAACATAACGAACTACTATCTAACTGAT   936

Query   913   TGGGAGTTCGGTACGGAATGGGGAACAATGACTTCCAATGGTACAGCCTACTTCTCATGG   972
               !!!!!!!! !! !! !!!!!!!!!!!! !!!!! !! !!!!!!!!!!! !! !!    !!!
Sbjct   937   TGGGAGTTTGGCACAGAATGGGGAACTATGACATCGAATGGTACAGCTTATTTTAGCTGG   996

Query   973   ACAATATCGAATTCTATGAAACTCTCCTCTAA    1005
               !! !!!    !! !! !! !!!!! !! !! !!!
Sbjct   997   ACTATAAGTAACTTTTACGAAACACTACTGTAA   1029
```

FIG. 2 (continued)

```
Query = SEQ ID NO: 1 - SSO1949 Wild Type from AE006641 - Length=1005
Subject = SEQ ID NO: 4 - SSO1949 optimized for expression in dicot plants -
Length=1029

Score =  742 bits (822),  Expect = 0.0
 Identities = 727/936 (78%), Gaps = 6/936 (1%)
 Strand=Plus/Plus Query  73    GCTATTTACCTACACCATCAGTCACCTAATGTCAAAACATCATCGATAACTGTCACCACT  132
             ||||| || ||||| ||||| || |||||||| |||||| || ||  || || ||| |||
Sbjct  97    GCTATATATCTACATCATCAATCCCCTAATGTAAAAACAAGCTCCATTACTGTGACGACT  156

Query  133   AACGAAACCACAACTTTAATGAGCATAACAACCAATACCGTACCTACAACAGTAACGCCC  192
             || ||||||||||| |||||| ||||| || || || || |||| ||||| ||| |||||
Sbjct  157   AATGAAACCACAACGTTAATGTCGATAACTACGAATACTGTCCCAACGACAGTTACCCCC  216

Query  193   ACTACATCTTCTATTCCTCAGCTAATCTATGTTACATCCTCTG---CTAGTTCACCAACT  249
             || ||  || || || || ||||||| ||  || || ||| |    |||||    |||||
Sbjct  217   ACCACTTCATCGATACCTCAGCTTATATACGTAACATCTTCAGCATCTAGT---CCAACT  273

Query  250   CCAGTTTATCTAAATAACTCAACTGTACCATCATTTTATCTTGAAGTCAACATGTGGAAT  309
             || || ||||| || || ||||||||| |||||| | |||||  |||| ||| |||||| 
Sbjct  274   CCCGTGTATCTCAACAATTCAACTGTCCCATCATTCTATCTAGAGGTCAATATGTGGAAC  333

Query  310   GCTAAAACTTGGAATGGCAACTATACCATGGTCTTTAACCCGCTTACTCGTACGCTCTCT  369
             || |||| |||| |||||   || || |||||  || || | || ||  ||  || |||
Sbjct  334   GCCAAAACATGGAACGGCAATTACACGATGGTATTTAATCCATTAACAAGAACTCTCAGC  393

Query  370   GTTAGTTTCAACTTAACGCAAGTTAATCCATTACAGTGGACTAATGGCTATCCGGAAATT  429
             ||      | ||  | ||  ||||| ||||| ||||| |||||| || |||||  |||||
Sbjct  394   GTGTCATTTAATCTGACTCAAGTAAATCCTTTACAGTGGACAAATGGATACCCTGAAATT  453

Query  430   TACGTGGGCAGAAAACCCTGGGATACTTCATATGCAGGTAACATATTCCCAATGAGGATA  489
             ||||| ||| ||||||| |||||||||   ||||||| || || ||| |||| |||| ||
Sbjct  454   TACGTTGGCAGGAAACCATGGGATACTAGTTATGCAGGAAATATTTTCCCGATGAGAATA  513

Query  490   GGCAATATGACACCGTTTATGGTATCGTTTACATAAACTTAACTAAGCTAGACCCGTCA  549
             |||||  ||||||||||||||||  | |||||||||||||| || ||  |||| ||||||
Sbjct  514   GGCAACATGACACCGTTTATGGTCAGCTTTTATATAAACTTAACAAAACTAGATCCGTCA  573

Query  550   ATAAATTTCGATATTGCGTCTGACGCTTGGATAGTTAGGCCTCAAATAGCATTTAGTCCC  609
             || ||  || ||||| || || || |||||||||| |||||||||| | ||  ||   |
Sbjct  574   ATTAACTTTGATATAGCATCGGATGCTTGGATAGTCAGGCCACAAATTGCTTTTTCACCA  633

Query  610   GGAACTGCTCCAGGTAATGGGGACATTGAGATAATGGTCTGGTTATTTAGTCAGAATTTA  669
             || || ||||| ||||| ||||||| || || || |||||||||||  ||||| || ||
Sbjct  634   GGGACAGCTCCCGGTAACGGCGACATCGAAATAATGGTCTGGTTATTCTCTCAGAACCTA  693
```

FIG. 3

```
Query  670  CAGCCTGCTGGGCAACAAGTTGGAGAAGTAGTAATCCCAATATATATTAATCACACTCTA  729
            ||||| || || ||  ||||| ||  ||||| |||||  ||||||||||| || || ||  |
Sbjct  694  CAGCCGGCGGGTCAGCAAGTCGGTGAAGTTGTAATACCAATATATATCAACCATACCTTG  753

Query  730  GTCAACGCCACTTTCCAAGTGTGGAAGATGAAGAACGTCCCATGGGGAGGTTGGGAGTAC  789
            || ||||| || ||||||||| ||||| |||||||| || ||  |||||||||||||||| |
Sbjct  754  GTTAACGCTACCTTCCAAGTCTGGAAAATGAAGAATGTACCTTGGGGAGGTTGGGAGTAT  813

Query  790  ATAGCATTTAGACCAGATGGCTGGAAAGTCACAAATGGTTACGTCGCATATGAGCCCAAC  849
            || |||||  | || ||  |||||||  || || |||||  || || || || ||| |||  |||
Sbjct  814  ATCGCATTCCGTCCGGACGGCTGGAAGGTTACTAATGGCTATGTGGCCTACGAGCCAAAC  873

Query  850  TTGTTCATCAAAGCGTTAAATAATTTCGCAAGCTACAACATTACAAACTATTACTTAACG  909
            || ||||||  || ||   ||||  ||||||||    |||| ||||  || |||||||||||  |
Sbjct  874  TTATTCATTAAGGCACTAAACAATTTCGCTTCATACAATATTACTAATTATTACTTAACT  933

Query  910  GATTGGGAGTTCGGTACGGAATGGGGAACAATGACTTCCAATGGTACAGCCTACTTCTCA  969
            || ||||||  |||||  ||  |||||||||| ||||||    |||||||||  || ||||||  |
Sbjct  934  GACTGGGAATTCGGAACTGAATGGGGCACTATCACAAGCAATGGTACTGCTTACTTCAGC  993

Query  970  TGGACAATATCGAATTTCTATGAAACTCTCCTCTAA         1005
            |||||||||:    ||  || |||||  || |||||  |||
Sbjct  994  TGGACAATAAGTAACTTTTATGAGACACTCCTTTAA         1029
```

FIG. 3 (continued)

```
Query = SEQ ID NO: 2 - CelA Wild Type from gi|13274206|emb|AJ308623.1 - Length=1778
Subject = SEQ ID NO: 5 - CelA optimized for expression in plants - Length=1637

Score = 1270 bits (1408),  Expect = 0.0
 Identities = 1244/1604 (78%), Gaps = 0/1604 (0%)
 Strand=Plus/Plus Query  148   CCGTCTCGCGTGCCCAAATCGATTTTTTATAATCAAGTTGGGTATCTGATCAGCGGCGAC  207
             ||||| || || || || || || |||||||| || || ||||| || || ||||| |||
Sbjct  21    CCGTCCCGTGTTCCTAAGTCTATCTTTTATAACCAGGTGGGGTACCTCATTAGCGGTGAC  80

Query  208   AAGCGCTTTTGGATTCAGGCTCACGAGCCTCAGCCTTTCCCGCTGCGCACGCCGGAAGGG  267
             ||| | || ||||||||||| |||||| || || || ||||| || || || ||||| |||
Sbjct  81    AAGAGGTTCTGGATTCAGGCGCACGAACCGCAACCGTTCGCTCTCCGTACTCCGGAGGGG  140

Query  268   CAGGCCGTGTTCGCGGGAATGACGAAGCCCGTCGGCGGGAATTGGTACGTCGGCGATTTT  327
             |||||||| |||| |||| || ||||| || ||||||||| || || ||||| || |||
Sbjct  141   CAGGCCGTTTTCGCCGGCATGACTAAACCCGTCGGAGGTAACTGGTATGTCGGAGACTTT  200

Query  328   ACCGCGCTTCGCGTGCCGGGGACCTACACGTTGACGGTAGGGACTCTCGAGGCGCGGGTC  387
             ||||| || |||||||| || |||||||| || || ||||| || || |||||||| ||
Sbjct  201   ACCGCCCTTCGCGTGCCTGGGACTTATACCCTGACGGTGGGTACCCTCGAGGCGCGTGTT  260

Query  388   GTTATCCATCGCCGCGCGTATCGTGACGTGCTCGAGGCCATGCTGCGCTTCTTCGACTAT  447
             || |||||  || | || || || || || || |||||||||| | ||| || |||||
Sbjct  261   GTCATCCACCGGAGAGCTTATCGCGATGTCTTGGAGGCCATGCTTCGTTTCTTCGACTAC  320

Query  448   CAGCTCTGCGGCGTCGTGCTGCCCCAGGATGAAGCCGGGCCGTGGGCGCACGGCGCCTCT  507
             ||| | || || |||||||| || |||||| ||||| ||||| ||| || ||||| |||
Sbjct  321   CAGTTGTGCGGGGTCGTGCTTCCGGAGGACGAGGCAGGCCCGTGGGCACACGGTGCATGC  380

Query  508   CACACGAGCGACGCCAAGGTGTTTGGCACCGAGCGCGCCTTGGCCTGCCCAGGCGGTTGG  567
             || ||   |||||| || |||||||| || ||||| ||  ||||| |||| ||| |||
Sbjct  381   CATACTTCCGACGCTAAAGTGTTTGGTACGGAGAGGGCATTGGCTTGCCCCGGCGGATGG  440

Query  568   CACGACGCTGGCGATTACGGCAAATACACGGTCCCCGCCGCCAAGGCCGTGGCCGATCTC  627
             || || || || || |||||||| || || ||||| || ||||||||||| || ||||||
Sbjct  441   CATGATGCGGGAGATTACGGCAAGTATACAGTGCCTGCTGCGAAGGCTGTGGCTGATCTC  500

Query  628   CTGCTCGCCACGAGTACTTCCCGGCGGCACTGGCGCACGTCCGCCCCATGCGCTCGGTG  687
             || || || || |||||||||||| || || ||| || ||| |||| ||||| || |||
Sbjct  501   CTCCTTGCTCATGAGTACTTCCCGGCCGCGTTGGCTCACGTGCGCCCTATGCGGTCCGTG  560

Query  688   CATCGGGCGCCTCATCTGCCGCCGGCGCTCGAGGTGGCGCGCGAGGAGATTGCCTGGCTT  747
             ||  | |||||| || |||| || || ||||||||||| || ||||| |||||| |||||
Sbjct  561   CACAGGGCGCCGCACCTGCCTCCCGCTCTGGAGGTCGCGAGGGAGGAAATTGCTTGCTT  620

Query  748   CTCACCATGCAGGATCCCGCGACAGGCGGCGTGTACCACAAAGTCACCACGCCTTCCTTT  807
             || || |||||||||||||| || || || |||||||||| || |||||||| || ||
Sbjct  621   TTGACCATGCAGGATCCCGCCACTGGGGGAGTTTACCACAACGTGACCACGCCGTCATTC  680
```

FIG. 4

```
Query   808   CCGCCGCTCGACACGCGCCCCGAAGACGACGATGCGCCCCTCGTCCTCAGTCCCATCTCC   867
              ||||| ||  |||| ||||| || || |||||||| || || ||||| || || ||||||
Sbjct   681   CCGCCTCTGGACACTCGCCCAGAGGATGACGATGCTCCGCTGGTCCTAAGCCCGATCTCC   740

Query   868   TACGCCGCCACGGCCACGTTTTGCGCCGCCATGGCGCATGCCGCCCTGGTGTACCGCCCT   927
              || || ||  ||||  | ||||| || || ||||||||||| |||| ||  || || ||
Sbjct   741   TATGCAGCAACGGCTACATTCTGTGCTGCCATGGCGCATGCTGCGCTCGTTTATCGTCCC   800

Query   928   TTCGATCCGGCCCTATCCTCGTGCTGTGCGGACGCCGCCCGTCGCGCGTACGCGTGGCTC   987
              ||||||||||||| | ||| |||  || || ||||||  || | ||  || ||| ||||
Sbjct   801   TTCGATCCGGCCCTGTCCTCATGTTGCGCGGATGCGGCCAGGAGGGCATACGCTTGGCTC   860

Query   988   GGCGCGCACGAGATGCAGCCGTTTCACAATCCCGATGGGATCCTCACGGGCGAATACGGC   1047
              || | ||||||||||||||| ||||||| |||||||||||| || ||||| ||| |||
Sbjct   861   GGTGCGCACGAGATGCAGCCATTTCACAACCCCGACGGGATTCTGACGGGTGAGTATGGC   920

Query   1048  GACGCGGAACTCCGCGACGAGCTGTTGTGGGCGTCCTGCGCCCTGCTTCGCATGACCGGC   1107
              || || ||||| ||||| ||||| || |||||  |     ||   ||   | ||| |||
Sbjct   921   GATGCCGAACTTCGCGATGAACTGCTATGGGCTAGCTGTGCGTTGCTCAGGATGACGGGC   980

Query   1108  GATTCCGCGTGGGCACGCGTGTGCGAGCCGCTTCTCGATCTCGACCTCCCGTGGGAGTTG   1167
              ||||| ||||||||  || |||||||  | ||  |||||| || || ||  |||| |
Sbjct   981   GATTCTGCGTGGGCTAGAGTTTGCGAACCTCTCCTGGATCTTGATTTGCCCTGGGAACTC   1040

Query   1168  GGATGGGCGGACGTCGCACTCTACGGCGTCATGGATTACCTGCGCACTCCGCGCGCCGCC   1227
              ||  ||||| |  || ||  ||  ||  | |||||||| || ||||||  ||| | |||
Sbjct   1041  GGGTGGGCAGATGTTGCTCTGTACGGTGTTATGGATTATCTGCGCACCCCCAGGGCTGCC   1100

Query   1228  GTATCGGACGACGTGCGAAACAAGGTGAAAACCCGCCTTCTCCGAGAACTCGACGCCCTC   1287
              ||      ||||| | || |||||||| |  ||||||||||| ||||||| || ||| 
Sbjct   1101  GTTAGTGACGATGTTAGGAACAAGGTCAAGTCCCGCCTTCTGAGAGAACTTGATGCCTTG   1160

Query   1288  GCCGCGATGGCTGAGTCGCATCCGTTCGGCATTCCCATGCGGGATGACGATTTCATCTGG   1347
              ||||| ||||| ||| || || || ||| || || || ||||| ||||| |||||||||
Sbjct   1161  GCCGCCATGGCAGAATCCCATCCATTTGGTATACCTATGCGGGACGATGACTTCATCTGG   1220

Query   1348  GGCAGCAACATGGTGCTCTTGAACCGCGCCATGGCGTTCCTGCTGGCCGAAGGCGTCGGT   1407
              |||   || |||||  | || |||| ||||||||| ||||| ||||||||| ||| |
Sbjct   1221  GGCTCTAATATGGTCCTTTTGAACCGGGCCATGGCTTTCCTCCTGGCAGAGGGCGTTGGC   1280

Query   1408  GTCCTTCATCCCGCTGCACATACGGTGGCCCAGCGCGCGGCGGACTACCTGTTTGGCGCA   1467
              ||  | || ||| |||| |||| || ||||||  || || ||||| ||||| |||||||
Sbjct   1281  GTGTTGCACCCTGCTGCCCATACTGTCGCCCAGAGAGCTGCCGACTATCTGTTCGGCGCA   1340

Query   1468  AATCCGCTCGGGCACTGCTACGTCACGGGCTTTGGCCAACGCCCCGTGCGCCATCCGCAT   1527
              || || ||  || ||  | ||||| | || || ||||| || |  || |||| ||||||
Sbjct   1341  AACCCCCTGGGTCAATGCTACGTGACAGGCTTCGGGCAGAGGCCGGTTAGGCACCCGCAT   1400

Query   1528  CATCGCCCGTCCGTCGCGGATGATGTGGACCATCCCGTCCCTGGCATGGTCGTCGGCGGC   1587
              ||||| || |  ||||| ||||||||||||||||||||  |||| ||||| || || ||
Sbjct   1401  CATCGGCCGAGCGTCGCAGATGACGTGGACCATCCGGTGCCTGGGATGGTGGTGGGGGGC   1460
```

FIG. 4 (continued)

```
Query  1588  CCAAACCGCCACCTGCAGGACGAGATCGCCCGCGCACAGCTTGCGGGGAGACCTGCGATG  1647
             ||  |||  |  ||  ||  ||  |||||  || |  ||||||||||  ||  |  ||  |  ||  |||
Sbjct  1461  CCCAACAGGCATCTTCAAGACGAAATTGCGCGCGCACAGCTAGCTGGCCGCCCAGCCATG  1520

Query  1648  GAGGCGTACATCGATCACCAGGACAGCTACTCGACCAACGAGGTCGCCGTCTACTGGAAT  1707
             ||  ||  ||||||||||||  |||||  |||||||||  ||||  |||||  ||||  |||||
Sbjct  1521  GAAGCCTACATCGATCATCAGGATAGCTACTCTACCAATGAGGTTGCCGTTTATTGGAAC  1580

Query  1708  TCGCCTGCCGTGTTTGTCATCGCGGCTTTGCTCGAGGCGCGCGG  1751
             |||||  ||  ||  ||  ||  ||  ||||||   |    |  ||||||  |||||
Sbjct  1581  TCGCCCGCGGTCTTCGTGATAGCGGCACTTTTGGAGGCCCGCGG  1624
```

FIG. 4 (continued)

SSO
1949
 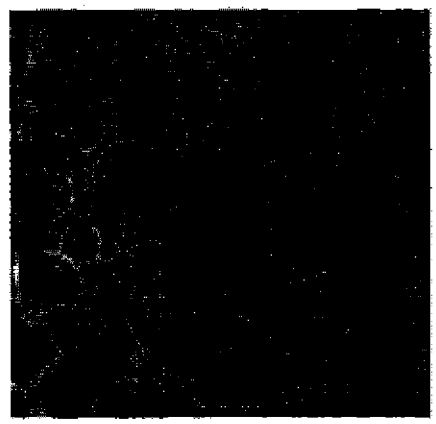
Wild
Type
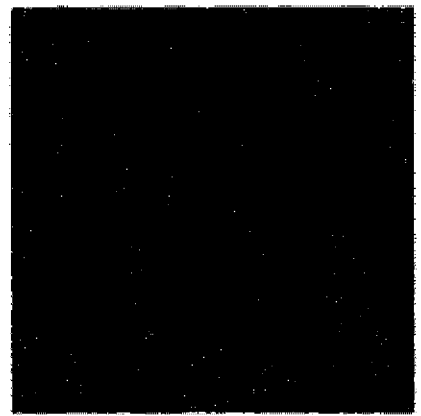 
FIG. 9

US 9,024,111 B1

METHODS AND MATERIALS FOR DECONSTRUCTION OF BIOMASS FOR BIOFUELS PRODUCTION

STATEMENT OF GOVERNMENT INTEREST

This invention was made with Government support under Government Contract No. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

FIELD OF INVENTION

This invention relates to the field of biofuel production, more specifically molecular genetics techniques for improved biofuel production.

BACKGROUND

Reducing the dependence of the United States on foreign energy supplies, specifically on imported petroleum is an important national security priority (DOE/USDA/EERE). The production of transportation fuels derived from biomass to displace fossil fuels is an important element of our national energy policy and the Department of Energy has set a goal to replace 30% of liquid petroleum transportation fuels with biofuels by 2025. Currently, almost all of domestic ethanol production is from corn-derived starch, which in itself is a high value energy food and feed commodity. An alternative is lignocellulosic biomass (e.g., grasses, wood, agriculture waste, etc.), which is renewable, cheap and readily available. Rice straw accounts for over half of the world's cultivated biomass, and is burned to waste, causing environmental problems (Kim and Dale, Biomass and Bioenergy 26 (2004) 361-375).

Dedicated energy crops (e.g., herbaceous materials and short rotation woody crops) and agricultural waste are frequently discussed as a preferred long-term feedstock solution for renewable, cheap, and globally available biofuels. The cellulosic and hemicellulosic components within these types of biomass are carbohydrate polymers that make up the walls of plant cells. Conversion of these polymers to fermentable sugars typically occurs with a two-step process:
1) Chemical pretreatment to disrupt cellulose, hemicellulose, and lignin cross-linking.
2) Exogenous recombinant microbial enzymes are added to hydrolyze cellulose and hemicellulose into 6- and 5-carbon sugars, respectively.

The current efficiency of this process is low due to the inherent recalcitrance of cellulosic biomass to these process steps, mass transfer issues during the deconstruction unit operations, and low activity of recombinant deconstruction enzymes. Costs are also high due to low net efficiency, the requirement for enzyme reagents, and energy intensive and cumbersome pretreatment steps.

In light of the above, improved methods of biofuel production are still needed, including improved methods of producing biofuels from lignocellulosic biomass.

SUMMARY OF INVENTION

In one aspect, the present invention relates to an isolated polynucleotide comprising a sequence at least about 80% identical to a sequence selected from the group consisting of SEQ ID NOs: 3-5. In certain examples, the invention relates to an isolated polynucleotide comprising a sequence at least about 81%, 82%, 83%, 84%, 85%, 86%, 87%, 88%, 89%, 90%, 91%, 92%, 93%, 94%, 95%, 96%, 97%, 98%, 99%, or 100% identical to a sequence selected from the group consisting of SEQ ID NOs: 3-5. In other examples, the invention relates to an isolated polynucleotide comprising a sequence selected from the group consisting of SEQ ID NOs: 3-5. In further examples, the isolated polynucleotide encodes a polypeptide at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to a peptide sequence selected from SEQ ID NOs: 13 and 14.

In another aspect, the invention relates to a vector comprising the isolated polynucleotides described herein. In certain examples, the vector further comprises a location-specific signal sequence, for instance, a signal sequence located adjacent to the isolated polynucleotide sequence in the vector. In other examples, the location-specific signal sequence comprises an apoplast-targeting sequence. In further examples, the apoplast-targeting sequence comprises a nucleic acid sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to the nucleic acid sequence of SEQ ID NO: 6.

In an additional aspect, the invention relates to a host cell transformed with a vector described herein. In further aspects, the invention relates to a plant comprising a transformed host cell described herein.

In yet another aspect, the invention relates to a method of producing a plant useful in the production of biofuels, the method comprising introducing into a plant cell one or more exogenous nucleic acids encoding a cellulosic degradation enzyme that shows increased activity at extreme pH or temperature, wherein each of said one or more exogenous nucleic acids comprise a nucleic acid sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to a sequence selected from the group consisting of SEQ ID NOs: 3-5. In certain examples, the one or more exogenous nucleic acids are obtained from an extremophile microorganism. In other examples, the exogenous nucleic acid encodes SSO1949. In further examples, the exogenous SSO1949 nucleic acid comprises a nucleic acid sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to a sequence selected from the group consisting of SEQ ID NOs: 3-4. In additional examples, the exogenous nucleic acid encodes Ce1A. In particular examples, the exogenous Ce1A nucleic acid comprises a nucleic acid sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 5. In other examples, the exogenous nucleic acid encodes a polypeptide that is at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 13 or 14.

In further examples, the method comprises introducing a first and a second exogenous nucleic acid, wherein the first exogenous nucleic acid encodes SSO1949 and comprises a nucleic acid sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to a sequence selected from the group consisting of SEQ ID NOs: 3-4, and the second exogenous nucleic acid encodes Ce1A and comprises a nucleic acid sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 5.

In additional examples, the exogenous nucleic acid further comprises a location-specific signal sequence. In particular examples, the location-specific signal sequence targets said cellulosic degradation enzyme to a plant's apoplast. In further examples, the location-specific signal sequence comprises a nucleic acid sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 6.

In yet another aspect, the invention relates to a plant useful for the production of biofuels, wherein the plant comprises one or more exogenous nucleic acids encoding a cellulosic degradation enzyme that shows increased activity at extreme pH or temperature. In certain examples, each of the one or more exogenous nucleic acids comprise a nucleic acid sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to a sequence selected from the group consisting of SEQ ID NOs: 3-5. In other examples, the one or more exogenous nucleic acids are obtained from an extremophile microorganism. In other examples, the exogenous nucleic acid encodes SSO1949. In further examples, the exogenous SSO1949 nucleic acid comprises a nucleic acid sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to a sequence selected from the group consisting of SEQ ID NOs: 3-4. In additional examples, the exogenous nucleic acid encodes Ce1A. In particular examples, the exogenous Ce1A nucleic acid comprises a nucleic acid sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 5. In further examples, the exogenous nucleic acid encodes a polypeptide that is at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 13 or 14.

In other examples, the plant comprises a first and a second exogenous nucleic acid, wherein the first exogenous nucleic acid encodes SSO1949 and comprises a nucleic acid sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to a sequence selected from the group consisting of SEQ ID NOs: 3-4, and the second exogenous nucleic acid encodes Ce1A and comprises a nucleic acid sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 5. In additional examples, the exogenous nucleic acid further comprises a location-specific signal sequence. In particular examples, the location-specific signal sequence targets said cellulosic degradation enzyme to a plant's apoplast. In certain other examples, the location-specific signal sequence comprises a nucleic acid sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 6.

BRIEF DESCRIPTION OF THE DRAWINGS

The foregoing summary, as well as the following detailed description, is further understood when read in conjunction with the appended figures. For the purpose of illustrating the invention, there is shown in the figures exemplary embodiments of the invention; however, the invention is not limited to the specific methods and devices disclosed herein. In the drawings:

FIG. 2 shows a sequence alignment between the wild-type *Solfolobus solfataricus* SSO1949 nucleic acid sequence (SEQ ID NO: 1) and the modified SSO1949 sequence that has been optimized for expression in monocot plants (SEQ ID NO: 3). The alignment was made using the web-based BLAST2 tool available from NCBI with the blastn algorithm with default settings and no low-complexity filter.

FIG. 3 shows a sequence alignment between the wild-type *Solfolobus solfataricus* SSO1949 nucleic acid sequence (SEQ ID NO: 1) and the modified SSO1949 sequence that has been optimized for expression in dicot plants (SEQ ID NO: 4). The alignment was made using the web-based BLAST2 tool available from NCBI with the blastn algorithm with default settings and no low-complexity filter.

FIG. 4 shows a sequence alignment between the wild-type *Alicyclobacillus acidocaldarius* Ce1A nucleic acid sequence (SEQ ID NO: 2) and the modified Ce1A sequence that has been optimized for expression in plants (SEQ ID NO: 5). The alignment was made using the web-based BLAST2 tool available from NCBI with the blastn algorithm with default settings and no low-complexity filter.

FIG. 9 illustrates an SEM analysis of *Brachypodium* wild-type and SSO1949 containing transgenic tissue, wherein the plant tissue was incubated under conditions for enzyme activation. Wild-type tissue appears to have no change while the transgenic tissue looses its structural integrity upon enzyme activation.

DETAILED DESCRIPTION

Figure 1:
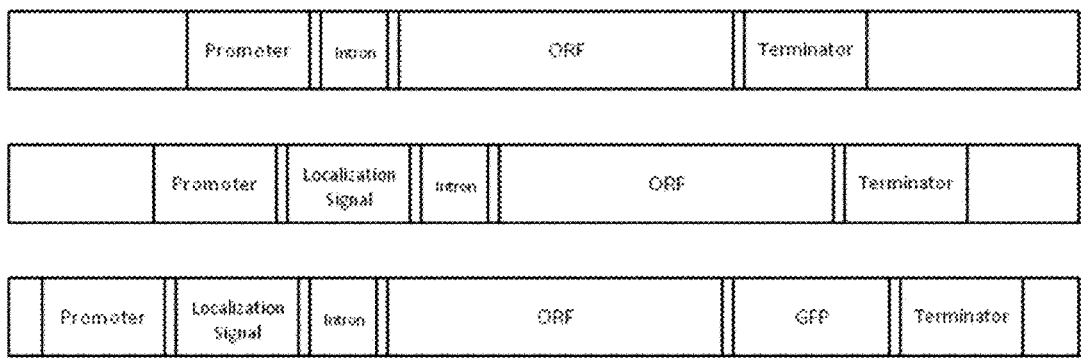
FIG. 1 shows the three basic constructs used for the transformations. The top construct provides cytoplasmic expression using a maize ubiquitin promoter, an intron, the selected open reading frame (ORF) to be expressed, and a terminator signal. The middle construct provides apoplast expression and includes a maize ubiquitin promoter, an apoplast localization signal, an intron, the selected ORF to be expressed, and a terminator signal. The bottom construct provides apoplast expression of the enzyme in conjunction with green fluorescent protein (GFP) for visualization of the product. This construct includes a maize ubiquitin promoter, an apoplast localization signal, an intron, the selected ORF to be expressed, a GFP-ORF fusion, and a terminator signal.

It is to be understood that this invention is not limited to particular embodiments, which can, of course, vary. It is also to be understood that the terminology used herein is for the purpose of describing particular embodiments only, and is not intended to be limiting. Further, all publications referred to herein are incorporated by reference herein for the purpose cited to the same extent as if each was specifically and individually indicated to be incorporated by reference herein.

As used in this specification and the appended claims, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule.

Additionally, as used herein, "comprising" is to be interpreted as specifying the presence of the stated features, integers, steps, or components as referred to, but does not preclude the presence or addition of one or more features, integers, steps, or components, or groups thereof. Thus, for example, a nucleic acid comprising a certain sequence may contain additional nucleic acid residues on the 5' or 3' end of the given sequence. Additionally, the term "comprising" is intended to include examples encompassed by the terms "consisting essentially of" and "consisting of" Similarly, the term "consisting essentially of" is intended to include examples encompassed by the term "consisting of"

Certain definitions used in the specification and claims are provided below. In order to provide a clear and consistent understanding of the specification and claims, including the scope to be given such terms, the following definitions are provided:

The term "actuator" means a DNA construct that encodes an exogenous enzyme using specific regulator elements that enable exogenous enzyme expression resulting in the hydrolysis of the plant's cell wall polysaccharides upon the initiation of some predetermined triggering event. In some embodiments, actuators are themselves exogenous polysaccharide hydrolysis enzymes. In certain embodiments, the actuator is an enzyme from an extremophile organism, and the triggering event is the change in environment to one in which the enzyme is typically active. For instance, if the enzyme is from an organism that is naturally found growing in extremely high temperatures, the triggering event may be increasing the temperature during processing of the plants to a similar temperature.

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods, such as the ligase chain reaction (LCR), and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like).

The term "exogenous" is intended to mean a gene or peptide which is not normally produced in a wild-type plant, or which is not normally produced in the given amount or in the given location within the wild-type plant.

The term "extremophile" or "extremophile organism" is intended to mean any organism capable of surviving in an extreme environment in comparison to the environmental conditions typical of the areas of the surface of the Earth in which life typically exists and thrives. Extreme environments can include extreme temperature (hot or cold), pressure (high or low), or pH (high or low).

With regard to nucleic acid and peptide sequences, "identity" or "percent identity" means the number of amino acid or nucleic acid residues that are identical between any two given sequences. Sequences that are not completely identical can still have the same function in certain cases, and persons skilled in the art are well aware of the types of substitutions that can be made without greatly impacting peptide function. For instance, if the number of non-identical residues is sufficiently small, the changes to the resulting peptide may be sufficiently minimal to have little or no effect on peptide function. Further, in some cases, a nucleic acid or amino acid mismatch is in the form of a "conservative mutation," meaning a mutation that results in the replacement of one amino acid for a different amino acid with similar chemical properties (such as replacing a leucine with an isoleucine). Further, at the nucleic acid level, a base change may result in no change in the ultimate amino acid sequence of the peptide, for example, in the case of a silent mutation resulting from the degeneracy of the genetic code.

The term "plant" includes reference to an immature or mature whole plant, including a plant from which seed or grain or anthers have been removed. Seed or embryo that will produce the plant is also considered to be the plant.

"Plant parts" means any portion or piece of a plant, including leaves, stems, buds, roots, root tips, anthers, seed, grain, embryo, pollen, ovules, flowers, cotyledons, hypocotyls, pods, flowers, shoots, stalks, tissues, tissue cultures, cells and the like.

"Polynucleotide," "polynucleotide sequence," "nucleic acid sequence," "nucleic acid fragment," and "oligonucleotide" are used interchangeably herein. These terms encompass nucleotide sequences and the like. A polynucleotide may be a polymer of RNA or DNA that is single- or double-stranded, that optionally contains synthetic, non-natural, or altered nucleotide bases. A polynucleotide in the form of a polymer of DNA may be comprised of one or more strands of cDNA, genomic DNA, synthetic DNA, or mixtures thereof.

"Primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are oligonucleotides from 10 to 30 nucleic acids in length, but longer or shorter sequences can be employed. Primers may be provided in double-stranded form, though the single-stranded form is preferred. A primer can further contain a detectable label, for example a 5' end or internal label.

"Transgenic plant" refers to a plant that comprises within its cells an exogenous polynucleotide. Generally, the exogenous polynucleotide is stably integrated within the genome such that the polynucleotide is passed on to successive generations. The exogenous polynucleotide may be integrated into the genome alone or as part of a recombinant expression cassette. "Transgenic" is used herein to refer to any cell, cell line, callus, tissue, plant part, or plant, the genotype of which has been altered by the presence of exogenous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

The term "vector" is used in reference to polynucleotide or other molecules that transfer nucleic acid segment(s) into a cell. A vector optionally comprises parts which mediate vector maintenance and enable its intended use (e.g., sequences necessary for replication, genes imparting drug or antibiotic resistance, a multiple cloning site, operably linked promoter/enhancer elements which enable the expression of a cloned gene, etc.). Vectors are often derived from plasmids, bacteriophages, or plant or animal viruses.

In one aspect, the present invention relates to a method for production of biofuels comprising introducing into a plant an exogenous actuator or set of actuators that enable the hydrolysis of the plant's cell wall polysaccharides. Such hydrolysis enzymes are well known in the art and any suitable enzyme can be employed herein. Suitable enzymes include endocellulase enzymes, exocellulase enzymes, beta-glycosidase, SSO1949, and Ce1A.

In certain embodiments, the actuators are produced, initiated, or activated only at a particular time or in response to a particular event or condition. This can be useful, for example, to ensure that the actuators are not activated during normal plant development, which could have a detrimental impact on the structural integrity of the cell wall and/or the viability of the plant. In certain embodiments, the genes encoding the actuators can be obtained from, or designed based upon, extremophile organisms. In certain embodiments, genes or peptides isolated from organisms capable of surviving in extremely high temperature or extremely acidic pH are utilized. Such extremophiles are well known in the art. In certain embodiments, such actuators remain inactive during the life cycle of the plant but become active during pretreatment that occurs at elevated temperatures, for example 90° C.-150° C. Such embodiments provide a unique thermal trigger within the biomass.

In other particular embodiments, the enzyme SSO1949 from *Sulfolobus solfotaricus* is employed. This enzyme can be described as a family 12 glycosyl hydrolase with a pH optimum of 1.8 and which exhibits no detectable activity below 60° C. In particular examples, SSO1949 can comprise a nucleic acid sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to the sequence of SEQ ID NO: 3 or 4. In other embodiments, the exogenous nucleic acid encodes a SSO1949 polypeptide that is at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 13.

In certain embodiments, the enzyme Ce1A from *Alicyclbacillus acidocaldarius* is employed. This enzyme can be described as a family 9, 1,4 glucanase with pH optimum of 4-5.5 and which exhibits no detectable activity below 55° C. In particular examples, Ce1A can comprise a nucleic acid sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to the sequence of SEQ ID NO: 5. In other embodiments, the exogenous nucleic acid encodes a Ce1A polypeptide that is at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 14.

In certain embodiments, the exogenous actuators are modified or manipulated at the sequence level prior to being introduced into the plant to optimize the sequence for expression in the target organism. Such modification or manipulation can, for example, identify and/or modify signals within the nucleic acid or peptide that may interfere with the production or activity of the actuator within the biofuel feedstock biomass, such as cryptic splice sites or targeting signals. Techniques for identifying such potentially-problematic signals are well known in the art and any suitable techniques can be used herein. In certain examples, the modifications to be made are identified via one or more of an intron/exon splice junction search, signal peptide search, protein targeting signal search, trans-membrane helix search, codon preference identification, or identification of contiguous codons. In certain examples, the nucleic acid sequences of wild-type Ce1A and/or SSO1949 were modified to remove bacterial targeting signals, cryptic splice sites, etc. from the sequences, thereby ensuring that the protein would not be improperly spliced or improperly targeted following expression of the peptides within the biofuel plant.

Additionally, in certain embodiments, it is desirable to systematically optimize the codon preferences for efficient transcription and translation within the target biofuel plant. Numerous codon optimization protocols and methods are well known in the art and any suitable protocol or method can be used herein. In certain examples, the codon optimization is accomplished using codon preference and frequency tables for the target plant. For example, in particular embodiments, Ce1A and SSO1949 are expressed in *Arabidopsis* and *Brachypodium* plants and are codon optimized for these plants prior to their introduction.

In certain other embodiments, the exogenous actuator is compartmentalized to a specific location in the plant cell. This can be accomplished, for example, by introducing the sequence in conjunction with a sequence that targets the peptide to a particular cellular location, for example the apoplast, or that causes the peptide to only be expressed in a certain portion of the plant, for instance the stalk, seeds, or leaves. Such targeting sequences are well known in the art, as are techniques for expressing a desired protein in conjunction with such a targeting sequence, and any suitable targeting sequence and method of production can be herein utilized. In certain embodiments, the targeting sequence comprises a nucleic acid sequence at least about 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 6.

The desired actuator nucleic acid sequences can be produced by any suitable techniques, including suitable recombinant and synthetic production techniques. Numerous suitable techniques are well known in the art.

In certain embodiments, the actuator nucleic acid sequence is introduced into a plant so that it can be stably incorporated into the plant's genome and expressed in an appropriate manner. Numerous techniques for introducing genetic material into a plant are well known in the art and any suitable technique can be used herein. Examples of suitable techniques include use of a particle inflow gun and *Agrobacterium* mediated transformation.

The success of the actuator introduction can be confirmed in any suitable manner, and numerous such methods for confirming the transcription or translation of a sequence are well known in the art, including PCR based assays, Southern blotting, or the use of a colorimetric or fluorescent tag on the peptide.

Following introduction of the actuator, digestion of the cellulosic mass can be initiated by growing the plants containing the actuator, harvesting the plants, and then processing the plants in a such a way as to cause expression or activation of the actuator. For example, if the actuator comprises an enzyme from an extremophile capable of surviving at high temperature, actuator activation can be accomplished by processing the harvested plant material at high temperatures. Similarly, if the actuator comprises an enzyme from an extremophile capable of surviving at acidic pH, actuator activation can be accomplished by processing the harvested plant material at such an acidic pH. In such cases, the high temperature or acidic pH will result in the accumulated actuator peptide undergoing a conformational change or protein refolding that results in the peptide converting from an inactive form to an active form.

The present invention is illustrated by the following examples. The foregoing and following description of the present invention and the various examples are not intended to be limiting, but rather are intended to be illustrative of the invention. Hence, it will be understood that the invention is not limited to the specific details of these examples.

EXAMPLES

Modification of Selected Actuators:

Two different actuators were identified for initial testing in the present method: Ce1A from *Alicyclbacillus acidocaldarius* and SSO1949 from *Sulfolobus solfotaricus*. The complete nucleic acid sequences of *Sulfolobus sofataricus* SSO1949 and *Alicyclobacillus acidocaldarius* Ce1A were obtained from public sequence repositories (See GenBank accessions gi|15896971:c1769048-1768044 from AE006641-*Solfolobus sofataricus* P2, complete genome and gi|13274206|emb|AJ308623.1|*Alicyclobacillus acidocaldarius* ce1A gene for cellulose; SEQ ID NOs: 1 and 2, respectively). To optimize these nucleic acid sequences for production in plants, numerous bioinformatics tools were employed, for example, to identify cryptic splice sites and leader sequences. Ce1A was optimized for production in plants generally, while SSO1949 was optimized separately for production in each of monocots and dicots. The optimization procedure involved identification and removal of cryptic splice sites and bacterial targeting signals, in addition to codon optimization for each of the target plants. However, it should be noted that the sequence changes employed were such that the ultimate amino acid sequence of the catalytic domain would remain the same as in the wild-type sequence. A comparison of the resulting optimized monocot and dicot nucleic acid sequences for SSO1949 (SEQ ID NOs: 3 and 4, respectively) versus the wild-type SSO1949 sequence (SEQ ID NO: 1) can be seen in FIGS. 2 and 3, respectively. The optimized nucleic acid sequences of SEQ ID NOs: 3 and 4 can produce the protein sequence of SEQ ID NO: 13 when expressed in the appropriate type of plant (monocot or dicot). A comparison of the resulting plant-optimized nucleic acid sequence for Ce1A (SEQ ID NO: 5) versus the wild-type Ce1A sequence (SEQ ID NO: 2) can be seen in FIG. 4. The optimized nucleic acid sequence of SEQ ID NO: 5 can produce the protein sequence of SEQ ID NO: 14 when expressed in a plant. The optimized SSO1949 and Ce1A sequences were then synthesized by a commercial nucleic acid synthesis facility (Blue Herron; Seattle, Wash.).

Additionally, a suitable targeting sequence was identified in order to allow for production and activation of the peptide in a specific location within the plant. More specifically, a targeting sequence that targets these actuator enzymes to the apoplast of the plant was identified (SEQ ID NO: 6). In certain examples, this targeting sequence was incorporated into the transformation vector upstream of the Ce1A or SSO1949 open reading frame to target production of the sequence to the apoplast of the plant (See FIG. 1).

Construction of Actuator:

All nucleic acid sequences were amplified by polymerase chain reaction and cloned into vectors obtained from collaborators at USDA or from Cambia (Australia). Standard molecular biology techniques were used according to Sambrook et al. (1986). All reagents were obtained from New England Biolabs (MA) and all chemicals were from Sigma chemicals (St Louis, Mich.). Integrity of the sequences was confirmed by sequencing using a commercial sequencing service and all sequence assembly was performed using Vector NTI. These optimized and/or targeted SSO1949 and Ce1A sequences were PCR amplified and cloned into three separate vector backbones: a monocot expression vector, a dicot expression vector, and a pBASK cassette containing vector. All monocot vectors were driven by a maize ubiquitin promoter containing an intron, while the dicot vector was under the control of the 35S promoter. Green fluorescent protein (GFP) was also cloned into some of the monocot and dicot vectors for visualization of the exogenous peptide (see FIG. 1 for the general cloning scheme of the expression vectors).

Transient Testing of the Actuator in *Brachypodium* and *Allium* Cells:

The actuators were introduced into *Allium sativa* epidermis cells (onion) and *Brachypodium sylvaticum* leaf tissue using a gold nano-particle based biolistics delivery device and expression of co-segregating beta-D glucuronidase (GUS) was assayed in order to determine actuator compatibility as well as expression levels and effects of surrogate gene on the host system. These tests demonstrated that the Ce1A actuator appears to express robustly both in onion and *Brachypodium* cells. However, the expression of SSO1949 was not as robust as expected, which could be due to cellular toxicity. A similar trend was also observed with SSO1949 in *Arabidopsis* lines.

Introduction of Actuator into *Arabidopsis*:

*Arabidopsis thaliana* Col-0 ecotype was used throughout this study. Seeds were stratified at 4° C. for 2 days to synchronize germination and then grown in Sunshine mix #1 (Sun Grow Horticulture Distribution, Bellevue Wash.) under 16 hour photoperiod at 22° C. in a greenhouse or on medium in a growth chamber with a 16 hour photoperiod, at constant temperature of 22° C. and a light intensity of 50 mE/m$^2$/s. *Agrobacterium tumefaciens* strain GV3101 were transformed using the dicot actuator constructs selected on antibiotic, and actuator-containing *agrobacterium* were used for floral dip transformation of *Arabidopsis* as previously described (Clough and Bent, 1998). Transformants were selected using antibiotics after 4-6 week and positive plants were tested for encoding genes by PCR. From this study, 6 lines of p35S-SSO1949 and 3 line of p35S-Ce1A were confirmed from a screening of ~20,000 SSO1949 seeds and 2000 Ce1A seeds. This discrepancy in the number of seeds screened is likely due to toxicity related issues with SSO1949 being driven by a strong 35S promoter. Additional Ce1A seed screening was performed to identify ten lines of Ce1A.

In order to obtain 10 lines of SSO1949 transformants, a pNOS-SSO1949 construct was designed and produced. The NOS promoter is a much weaker promoter, thereby greatly reducing the toxicity of SSO1949 in planta. Screening of the pNOS-SSO1949 was performed until 10 stably transformed clones were identified. The ten each SSO1949 and Ce1A clones were then characterized by molecular and enzymatic techniques.

Introduction of Actuator into *Brachypodium*:

Immature *Brachypodium* embryos were excised and used to introduce the actuators into *Brachypodium* cells. *Agrobacterium* was used for this transformation (typically a 6-8 month cycle). Several hundred stably transformed putative plantlets encoding SSO1949 and Ce1A were selected and evaluated by PCR and RT-PCR for expression of the transgenes. Shoot generation from the tissue appeared to be the easiest part of the regeneration process. Most of the shoots were unable to set seed and were lost in culture. The next highest losses were observed in the acclimatization of tissue to greenhouse conditions. In total 24 SSO1949 containing plants and 7 Ce1A containing plants were characterized both for gene expression and enzymatic activity.

Polymerase Chain Reaction (PCR) Analysis and Reverse Transcription PCR (RT-PCR) Analysis of Putative Stable Transgenics:

For PCR analysis of potential SSO1949 stable transgenics, genomic DNA was extracted by grinding a single leaf in 400 mL of buffer (200 mM Tris HCl pH 7.5, 250 mM NaCl, 25 mM EDTA, 0.5% SDS). After centrifugation, the isopropanol precipitated pellet was washed with 70% ethanol and resuspended in 50 μl of $H_2O$. 2 μL of genomic DNA in 25 μL volume was used per PCR reaction. The two primers that were used for amplification of SSO1949 were SSO F60 5'-CGTCAAGACCAGTAGTATTACCGTTACAACG-3' (SEQ ID NO: 7) and SSO R60 5'-CACGTAGCCGTTCGTAACCTTCC-3' (SEQ ID NO: 8). Resulting PCR products were resolved by gel electrophoresis through a 1.2% agarose gel and visualized by Ethidium Bromide staining.

For RT-PCR analysis of potential SSO1949 stable transgenics, total RNA was extracted from stably transformed *Arabidopsis* plant tissue using Qiagen RNA-easy plant mini extraction kit (Valencia, Calif.) according to the manufacturer's recommendations. Random hexamers were used to synthesize cDNA using a complete cDNA synthesis kit (Clontech, CA) according to the manufacturer's recommendations and samples were normalized to a final concentration of 500 ng/μL. Amplification was performed using Roche DNA Taq polymerase and was run according to the following conditions: 2 min at 94° C.; then 30 amplification cycles with 30 sec at 94° C., 1 min at 55° C., 3 mM at 72° C.; and a final extension time for 5 min at 70° C. The primers used for Ce1A, which produced a 576 bp product, were as follows Forward primer: 5'-cgtcccgtgttcctaagtct-3' (SEQ ID NO: 9)

Reverse primer: 5'-aacggcaacctcattggtag-3' (SEQ ID NO: 10)

The primers for SSO1949, which produced a 713 bp product, were as follows:

Forward primer: 5'-cgttacaacgaacgagacca-3' (SEQ ID NO: 11)

Reverse primer: 5'-cacgtagccgttcgtaacct-3' (SEQ ID NO: 12)

The products were separated on a 1.2% agarose gel.

These studies demonstrated the presence and transcription of the exogenous nucleic acids in the transgenic plants.

Total Soluble Proteins Extraction:

Total soluble protein (TSP) extraction from leaf tissues was performed using a slight modification from the technique described by Ziegelhoffer et al. (*Molecular Breeding* (2001) 8:147-158). Briefly, 100 mg fresh leaf plant sample was ground in liquid nitrogen to a fine powder using mortar and pestle and the powder was resuspended in sodium acetate grinding buffer (50 mM sodium acetate pH 5.5, 100 mM NaCl, 10% v/v glycerol, 0.5 mM ethylenediaminetetra-acetic acid (disodium salt), 1 mM phenylmethyl-sulfonyl fluoride, 1 mg/L aprotinin, 1 mg/L leupeptin, 1 mg/L pepstatin) at a ratio of 5 μL per mg of sample. Soluble extract was recovered from insoluble debris by centrifugation for 5 min in a microfuge at full speed. A solution of saturated ammonium sulfate was added to the extracts to achieve a final concentration of 2.7 M ammonium sulfate, followed by incubation on ice for 30 min, the resulting precipitate was recovered by centrifugation for 5 min. The ammonium sulfate pellet was resuspended in 5 μL of grinding buffer for each 2 μL of starting crude extract. Extracts were quantified using the Bradford method using a standard curve generated from bovine serum albumin (BSA).

Protein Extraction and Heat Fractionation:

Transformed plant sample were ground in liquid nitrogen to a fine powder using mortar and pestle. The powder was resuspended in extraction buffer (100 Mm Tris pH7.5, 1 M NaCl and 5% glycerol) and the slurry transferred to a 50 mL falcon tube and vortexed for 2 minutes. The suspension was centrifuged at maximum speed in a tabletop centrifuge and the supernatant was transferred to a new tube and incubated at 70° C. for one hour, followed by an additional centrifugation at maximum speed for 10 minutes. The supernatant was concentrated using a centricon with 10 Kd cut-off (Fisher Scientific) and the proteins quantified using a micro BCA assay (Fisher Scientific) according to the manufacturer's guidelines. Samples were normalized and three concentrations were used to setup saccharification assays in 100 mM K Phosphate pH 1.8 and 1.25% CMC for 20 hrs at 80° C. At the end of the saccharification reaction, 1 pL of 10N NaOH was added to each well to change the pH of the sample. Half of the saccharification reaction (50 pL) was transferred to a new tube and mixed with to equal volume of DNS reagent and incubated at 70° C. for 30 minutes.

DNS Reducing Sugar Assay:

The DNS Reducing Sugar Assay was used as a first pass to assay for enzyme activity. This assay is based on the presence of free carbonyl group (C=O), the so-called reducing sugars (aldehyde functional group present in glucose and the ketone functional group in fructose). In their presence and simultaneously, 3,5-dinitrosalicylic acid (DNS) is reduced to 3-amino,5-nitrosalicylic acid under alkaline conditions. It is suspected that there are many side reactions, and the actual reaction stoichiometry is quite complicated. The type of side reaction is dependent on the nature of the reducing sugars. Different sugar types result in varying color intensities; thus, the assay has to be calibrated for each sugar. In addition to the oxidation of the carbonyl groups in the sugar, other side reactions such as the decomposition of sugar also competes for the availability of 3,5-dinitrosalicylic acid. As a consequence, carboxymethyl cellulose can affect the calibration curve by enhancing the intensity of the developed color. Although this is a convenient and relatively inexpensive method, due to the relatively low specificity, one must run blanks diligently if the colorimetric results are to be interpreted correctly and accurately. When the effects of extraneous compounds are not known, one can effectively include a so-called internal standard by first fully developing the color for the unknown sample; then, a known amount of sugar is added to this sample. Because of the above issues, a number of blanks as well as recombinant enzyme purified control reactions were run alongside all test samples in the assay. Both for Ce1A as well as SSO1949, increases in enzyme activity were observed, but at varying levels (See FIG. 5). Looking at FIG. 5, the amount of reducing sugars following the enzymatic step in comparison to wild-type levels is illustrated. Wild-type levels of reducing sugars were set at 100% and the actuator-containing plants are calculated as percentage of wild-type. This variation in activity had a strong correlation with the RT-PCR results. The combined data indicated that the enzyme expression was a function of message abundance and the integration site of the actuator into the host genome.

To perform the DNS assay, DNS assay reagent was prepared as follows for each 100 mL solution: mixed 1 g of DNS (Sigma # D0550) in 50 mL of $H_2O$, stirred to dissolve at 40° C. 30 g of KNa Tartrate (Sigma #S2377) and 20 mL of 2N NaOH (J. T. Baker #3727-01) were subsequently added. The solution was brought to final volume with $H_2O$ and stored in brown ample bottle at room temperature. Saccharification samples in 96-well PCR plate were cooled to room temperature. If the samples were in acidic condition (pH<5.5), a small amount of 10N NaOH was added to each sample to bring its pH into an alkaline environment. 50 pL of samples were transferred to a new PCR plate containing 50 pL of DNS reagent. The plates were mixed well and quick spun down to prevent bubbles. For the standard curve, 10 mM D-glucose, 1:2 serial dilutions, were used. Plates were sealed and incubated for 30 minutes at 70° C. After incubation, the assay plate was spun down at 2000 RPM for 15 min. 95 pL of each reaction was transferred to Costa 96-well, black, clear bottom for reading absorbance at 540 nm.

EnzyChrom Glucose Assay:

The EnzyChrom Glucose Assay kit (EBGL-100) was obtained from BioAssay Systems and utilized as per the manufacturer's colorimetric protocol. This assay is a simple, direct, and high-throughput assay for measuring glucose concentrations. The BioAssay glucose assay kit uses a single working reagent that combines the glucose oxidase reaction and color reaction in one step. The assay can be run in an absorbance or fluorescence format. The color intensity of the reaction product at 570 nm or fluorescence intensity at EXem/ex=585/530 nm is directly proportional to glucose concentration in the sample. The assay utilizes as little as 20 µL sample and the linear detection range in 96-well plate is 5 to 600 RM glucose for colorimetric assays and 1 to 30 RM for fluorometric assays. This assay is quite specific and does not suffer form the background issues of the DNS assay.

Figure 5:
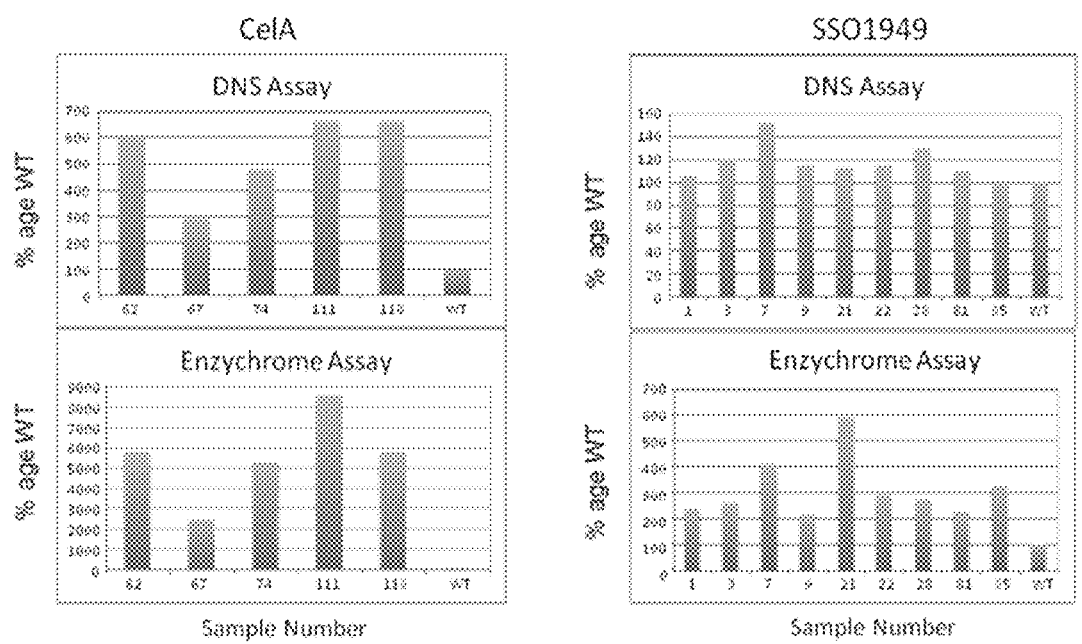
FIG. 5 illustrates the SSO1949 and Ce1A enzymatic activity from experiments conducted in *Arabidopsis* and *Brachypodium*, respectively, wherein total protein was extracted from transgenic plants and compared to enzyme activity levels in wild-type plants.
Figure 6:
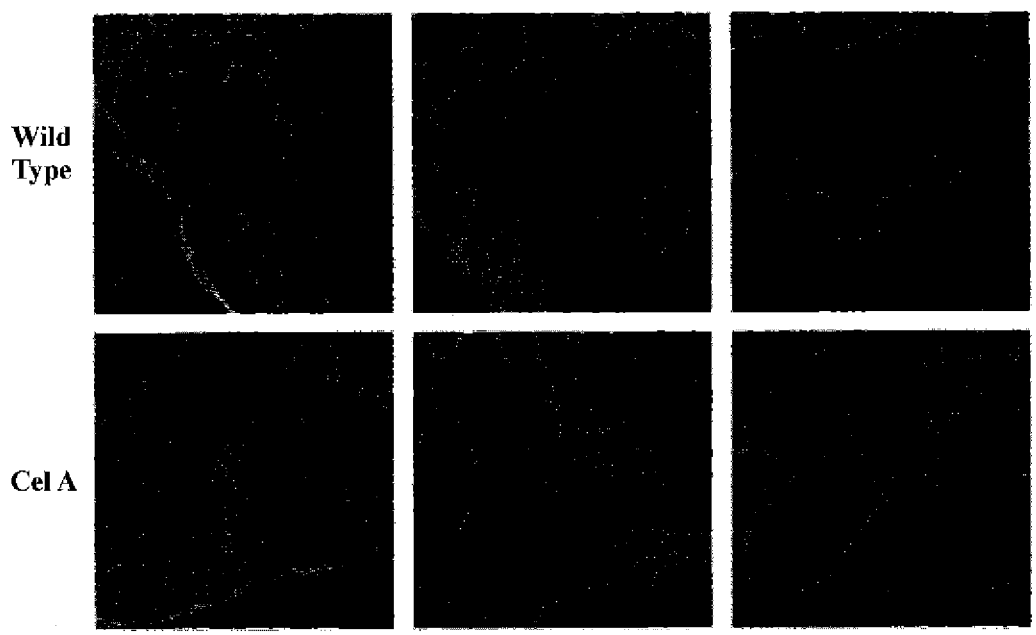
FIG. 6 shows an SEM analysis of *Arabidopsis* wild-type and Ce1A containing transgenic tissue, wherein the plant tissue was incubated under conditions for enzyme activation. Wild-type tissue appears to have no change while the transgenic tissue loses its structural integrity upon enzyme activation.
Figure 7:
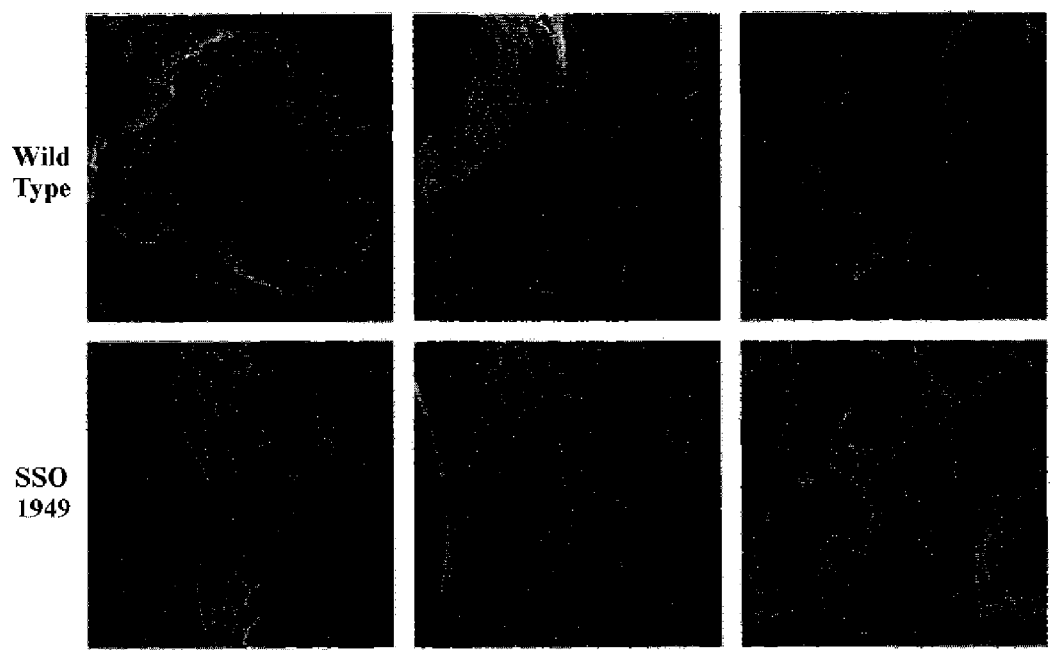
FIG. 7 illustrates an SEM analysis of *Arabidopsis* wild-type and SSO1949 containing transgenic tissue, wherein the plant tissue was incubated under conditions for enzyme activation. Wild-type tissue appears to have no change while the transgenic tissue loses its structural integrity upon enzyme activation.
Figure 8:
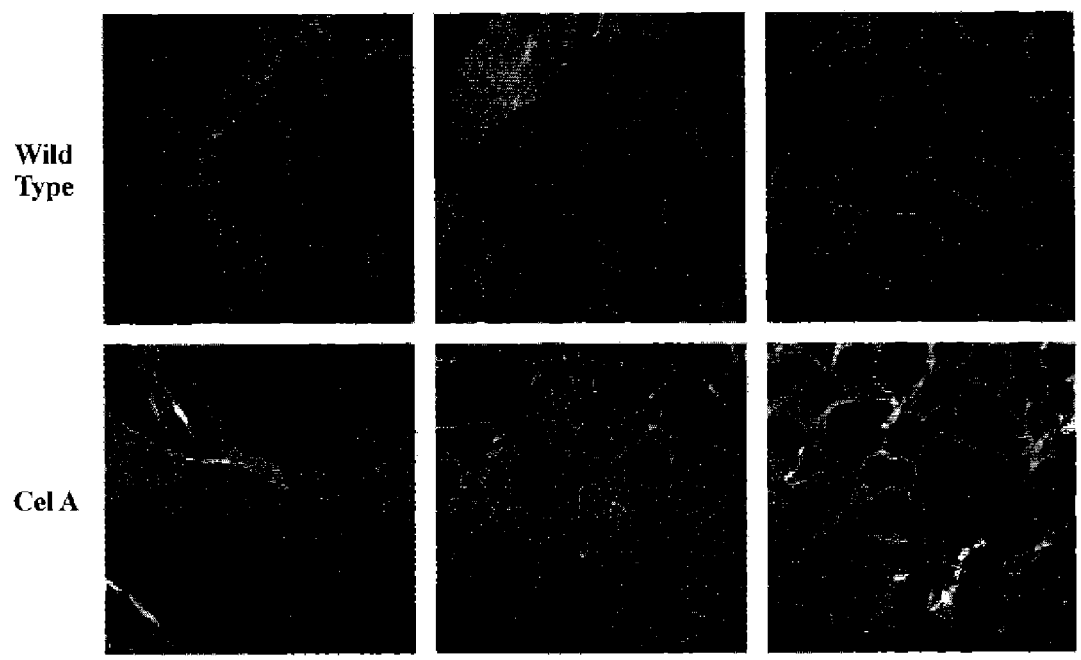
FIG. 8 illustrates SEM Analysis of *Brachypodium* wild-type and Ce1A containing transgenic tissue, wherein the plant tissue was incubated under conditions for enzyme activation. Wild-type tissue appears to have no change while the transgenic tissue looses its structural integrity upon enzyme activation.

Briefly, all components were equilibrated to room temperature and 20 µL of standards or saccharification samples were placed into the wells of a Costar 96-well, black, clear bottom plate. In each well, 80 µL of working reagent (85 µL of Assay Buffer, 1 µL of Enzyme Mix and 1 µL of Dye Reagent) was added and mixed well. Standards were prepared with provided Glucose, starting from 300 pM, 1:2 serial dilutions. The plate was spun down to eliminate bubbles and the reaction was incubated for 30 min at room temperature, followed by an absorbance reading at 570 nm. All samples screened by DNS were also screened with the EnzyChrome assay (FIGS. 5).

Scanning Electron Microscopy:

Actively growing stem tissues was harvested from the greenhouse and first embedded into 8% agarose in water for stability and then sliced into 100 micron thick sections using a Leica VT1000S vibratome (Leica Microsystems, Wetzlar, Germany). The sections were picked up from the water and directly transferred onto brass sample stubs. The pretreatment was done on these sample stubs with drops of either 1.2% (w/w) sulfuric acid for SSO samples or reaction buffer for Ce1A samples, or water as a control for both. Samples were incubated in an oven for 1 and 3 hrs at 70° C., keeping them under a moist atmosphere using wet filter paper to avoid evaporation of the drops.

After pretreatment the sample stubs with the pretreated plant sections were washed twice with PBS, fixed for 2 hrs in 2.5% Glutaraldehyde, washed again twice with PBS and dehydrated with subsequent Ethanol steps (30%, 50%, 70%, 80%, 90%, 3×100%), followed by critical point drying (using an Autosamdri-815, Tousimis, Rockville, Md., USA). The samples were then sputter coated with approximately 30 Angstrom of Au/Pd. Subsequently images were acquired with a 10 kV accelerating voltage using a Hitachi S-5000 microscope (Hitachi America, Terrytown, N.Y., USA) at up to 25,000× magnification.

Both the Ce1A and the SSO1949 plants appear to lose cellular integrity once the enzymes are activated but no gross structural changes were observed in the control samples (FIGS. 6-9). Looking at FIGS. 6-9, the left-most panel is an SEM image of stem tissue sections from wild-type or actuator-containing plants that have not been subjected to conditions that activate the enzyme. As these images illustrate, little to no subcellular, morphological or ultra-structure differences are observable between the wild-type and actuator-containing tissue. The middle and right most panels are stem tissue sections from wild-type or actuator-containing plants that have been subjected to conditions where the enzyme is activated. As these images illustrate, the wild-type tissue remains essentially the same as the non-treated controls, while the actuator-containing tissue loses its structural integrity and cell walls begin to collapse.

We claim:

1. An isolated polynucleotide comprising a sequence of at least 90% identical to a sequence selected from the group consisting of SEQ ID NOs: 3-5,
   wherein the isolated polynucleotide encodes a polypeptide that is at least 95% identical to SEQ ID NO: 13 or 14, and
   wherein the isolated polynucleotide encodes an exogenous enzyme that hydrolyzes a plant's cell wall polysaccharides.

2. The isolated polynucleotide of claim 1, wherein said polynucleotide comprises a sequence at least 95% identical to a sequence selected from the group consisting of SEQ ID NOs: 3-5.

3. The isolated polynucleotide of claim 1, wherein said polynucleotide comprises a sequence at least 99% identical to a sequence selected from the group consisting of SEQ ID NOs: 3-5.

4. The isolated polynucleotide of claim 1, wherein said polynucleotide comprises a sequence selected from the group consisting of SEQ ID NOs: 3-5.

5. A vector comprising the polynucleotide sequence of claim 1.

6. The vector of claim 5, wherein said vector further comprises a location-specific signal sequence adjacent to said isolated polynucleotide sequence.

7. The vector of claim 6, wherein said a location-specific signal sequence comprises an apoplast-targeting sequence.

8. The vector of claim 7, wherein said apoplast-targeting sequence comprises a nucleic acid sequence at least 90% identical to SEQ ID NO: 6.

9. A host cell transformed with the vector of claim 8.

10. A plant comprising the host cell of claim 9.

11. A method of producing a plant useful in the production of biofuels, said method comprising:
   introducing into a plant cell one or more exogenous nucleic acids encoding a cellulosic degradation enzyme that shows increased activity at extreme pH or temperature, wherein each of said one or more exogenous nucleic acids comprise a nucleic acid sequence at least 90% identical to a sequence selected from the group consisting of SEQ ID NOs: 3-5, wherein the nucleic acid sequence encodes a polypeptide that is at least 95% identical to SEQ ID NO: 13 or 14, and wherein the nucleic acid sequence encodes the cellulosic degradation enzyme that hydrolyzes a plant's cell wall polysaccharides.

12. The method of claim 11, wherein said one or more exogenous nucleic acids are obtained from an extremophile microorganism.

13. The method of claim 11, wherein said exogenous nucleic acid encodes a polypeptide that is at least 95% identical to SEQ ID NO: 13, and wherein said exogenous nucleic acid comprises a nucleic acid sequence at least 90% identical to a sequence selected from the group consisting of SEQ ID NOs: 3-4.

14. The method of claim 11, wherein said exogenous nucleic acid encodes a polypeptide that is at least 95% identical to SEQ ID NO: 14, and wherein said exogenous nucleic acid comprises a nucleic acid sequence at least 90% identical to SEQ ID NO: 5.

15. The method of claim 11, wherein said method comprises introducing a first and a second exogenous nucleic acid, wherein said first exogenous nucleic acid encodes a polypeptide that is at least 95% identical to SEQ ID NO: 13 and comprises a nucleic acid sequence at least 90% identical to a sequence selected from the group consisting of SEQ ID NOs: 3-4, and wherein said second exogenous nucleic acid encodes a polypeptide that is at least 95% identical to SEQ ID NO: 14 and comprises a nucleic acid sequence at least 90% identical to SEQ ID NO: 5.

16. The method of claim 11, wherein said exogenous nucleic acid further comprises a location-specific signal sequence.

17. The method of claim 16, wherein said location-specific signal sequence targets said cellulosic degradation enzyme to a plant's apoplast.

18. The method of claim 17, wherein said location-specific signal sequence comprises a nucleic acid sequence at least 90% identical to SEQ ID NO: 6.

19. A plant useful for the production of biofuels, wherein said plant comprises one or more exogenous nucleic acids encoding a cellulosic degradation enzyme that shows increased activity at extreme pH or temperature, wherein each of said one or more exogenous nucleic acids comprise a nucleic acid sequence at least 90% identical to a sequence selected from the group consisting of SEQ ID NOs: 3-5, wherein the nucleic acid sequence encodes a polypeptide that is at least 95% identical to SEQ ID NO: 13 or 14, and wherein the nucleic acid sequence encodes the cellulosic degradation enzyme that hydrolyzes a plant's cell wall polysaccharides.

20. The plant of claim 19, wherein said one or more exogenous nucleic acids are obtained from an extremophile microorganism.

21. The plant of claim 19, wherein said exogenous nucleic acid encodes a polypeptide that is at least 95% identical to SEQ ID NO: 13, and wherein said exogenous nucleic acid comprises a nucleic acid sequence at least 90% identical to a sequence selected from the group consisting of SEQ ID NOs: 3-4.

22. The plant of claim 19, wherein said exogenous nucleic acid encodes a polypeptide that is at least 95% identical to SEQ ID NO: 14, and wherein said exogenous nucleic acid comprises a nucleic acid sequence at least 90% identical to SEQ ID NO: 5.

23. The plant of claim 19, wherein said plant comprises a first and a second exogenous nucleic acid, wherein said first exogenous nucleic acid encodes a polypeptide that is at least 95% identical to SEQ ID NO: 13 and comprises a nucleic acid sequence at least 90% identical to a sequence selected from the group consisting of SEQ ID NOs: 3-4, and wherein said second exogenous nucleic acid encodes a polypeptide that is at least 95% identical to SEQ ID NO: 14 and comprises a nucleic acid sequence at least 90% identical to SEQ ID NO: 5.

24. The plant of claim 19, wherein said exogenous nucleic acid further comprises a location-specific signal sequence.

25. The plant of claim 24, wherein said location-specific signal sequence targets said cellulosic degradation enzyme to a plant's apoplast.

26. The plant of claim 25, wherein said location-specific signal sequence comprises a nucleic acid sequence at least 90% identical to SEQ ID NO: 6.

27. The isolated polynucleotide of claim 1, wherein the isolated polynucleotide encodes a polypeptide that is at least 95% identical to SEQ ID NO: 13 or 14.

28. A plant useful for the production of biofuels, wherein said plant comprises one or more exogenous nucleic acids encoding a cellulosic degradation enzyme that shows increased activity at extreme pH or temperature, wherein each of said one or more exogenous nucleic acids comprise a nucleic acid sequence at least 90% identical to a sequence selected from the group consisting of SEQ ID NOs: 3-4, wherein the nucleic acid sequence encodes a polypeptide that is at least 95% identical to SEQ ID NO: 13, and wherein the nucleic acid sequence encodes the cellulosic degradation enzyme that hydrolyzes a plant's cell wall polysaccharides.

29. The plant of claim 28, wherein the plant is a dicot, wherein the nucleic acid sequence comprises a sequence of at least 90% identical to SEQ ID NO: 4, and wherein the nucleic acid sequence encodes a polypeptide that is at least 95% identical to SEQ ID NO: 13.

30. An isolated polynucleotide comprising a sequence of at least 90% identical to a sequence selected from the group consisting of SEQ ID NOs: 3-5,
   wherein the isolated polynucleotide encodes a polypeptide that is at least 90% identical to SEQ ID NO: 13 or 14, and
   wherein the isolated polynucleotide encodes an exogenous enzyme having a glycosyl hydrolase activity observed in a wild-type SSO1949 enzyme or encodes an exogenous enzyme having a 1,4 glucanase activity observed in a wild-type Cel A enzyme.

31. The plant of claim 28, wherein the plant is a monocot, wherein the nucleic acid sequence comprises a sequence of at least 90% identical to SEQ ID NO: 3, and wherein the nucleic acid sequence encodes a polypeptide that is at least 95% identical to SEQ ID NO: 13.

\* \* \* \* \*

SEQUENCE LISTING

```
<160> NUMBER OF SEQ ID NOS: 14

<210> SEQ ID NO 1
<211> LENGTH: 1005
<212> TYPE: DNA
<213> ORGANISM: Sulfolobus solfataricus

<400> SEQUENCE: 1
atgataatga ataaattata tatcattata gttccgataa ttgtaataat agttgtgggt      60
gtaattggtg gagctattta cctacaccat cagtcaccta atgtcaaaac atcatcgata     120
actgtcacca ctaacgaaac cacaacttta atgagcataa caaccaatac cgtacctaca     180
acagtaacgc ccactacatc ttctattcct cagctaatct atgttacatc ctctgctagt     240
tcaccaactc cagtttatct aaataactca actgtaccat cattttatct tgaagtgaac     300
```

```
atgtggaatg ctaaaacttg gaatggcaac tataccatgg tctttaaccc gcttactcgt    360
acgctctctg ttagtttcaa cttaacgcaa gttaatccat tacagtggac taatggctat    420
ccggaaattt acgtgggcag aaaaccctgg gatacttcat atgcaggtaa catattccca    480
atgaggatag gcaatatgac accgtttatg gtatcgtttt acataaactt aactaagcta    540
gacccgtcaa taaatttcga tattgcgtct gacgcttgga tagttaggcc tcaaatagca    600
tttagtcccg gaactgctcc aggtaatggg gacattgaga taatggtctg gttatttagt    660
cagaatttac agcctgctgg gcaacaagtt ggagaagtag taatcccaat atatattaat    720
cacactctag tcaacgccac tttccaagtg tggaagatga agaacgtccc atggggaggt    780
tgggagtaca tagcatttag accagatggc tggaaagtca caaatggtta cgtcgcatat    840
gagcccaact tgttcatcaa agcgttaaat aatttcgcaa gctacaacat tacaaactat    900
tacttaacgg attgggagtt cggtacggaa tggggaacaa tgacttccaa tggtacagcc    960
tacttctcat ggacaatatc gaatttctat gaaactctcc tctaa                  1005

<210> SEQ ID NO 2
<211> LENGTH: 1778
<212> TYPE: DNA
<213> ORGANISM: Alicyclobacillus acidocaldarius

<400> SEQUENCE: 2
cggtgccggc cgacgttcgc ggcgcgcgcg cgggtcgcca tcgagcggat ggtggccatc     60
ggctgacgtc gagaggcgga ggcaggtatc ggcacgcgag gcgtcgaatc ctctctcctg    120
caagccggtg ggaggggatt cgacatgccg tctcgcgtgc ccaaatcgat tttttataat    180
caagttgggt atctgatcag cggcgacaag cgcttttgga ttcaggctca cgagcctcag    240
cctttcgcgc tgcgcacgcc ggaagggcag gccgtgttcg cgggaatgac gaagcccgtc    300
ggcgggaatt ggtacgtcgg cgatttttacc gcgcttcgcg tgccggggac ctacacgttg    360
acggtaggga ctctcgaggc gcgggtcgtt atccatcgcc gcgcgtatcg tgacgtgctc    420
gaggccatgc tgcgcttctt cgactatcag ctctgcggcg tcgtgctgcc cgaggatgaa    480
gccgggccgt gggcgcacgg cgcctgtcac acgagcgacg ccaaggtgtt tggcaccgag    540
cgcgccttgg cctgcccagg cggttggcac gacgctggcg attacggcaa atacacggtc    600
cccgccgcca aggccgtggc cgatctcctg ctcgcccacg agtacttccc ggcggcactg    660
gcgcacgtcc gccccatgcg ctcggtgcat cgggcgcctc atctgccgcc ggcgctcgag    720
gtggcgcgcg aggagattgc ctggcttctc accatgcagg atcccgcgac aggcggcgtg    780
taccacaaag tcaccacgcc ttcctttccg ccgctcgaca cgcgccccga agacgacgat    840
gcgcccctcg tcctcagtcc catctcctac gccgccacgg ccacgttttg cgccgccatg    900
gcgcatgccg ccctggtgta ccgccctttc gatccggccc tatcctcgtg ctgtgcggac    960 gccgccgtc gcgcgtacgc gtggctcggc gcgcacgaga tgcagccgtt tcacaatccc   1020
gatgggatcc tcacgggcga atacggcgac gcggaactcc gcgacgagct gttgtgggcg   1080
tcctgcgccc tgcttcgcat gaccggcgat tccgcgtggg cacgcgtgtg cgagccgctt   1140
ctcgatctcg acctcccgtg ggagttggga tgggcggacg tcgcactcta cggcgtcatg   1200
gattacctgc gcactccgcg cgccgccgta tcggacgacg tgcgaaacaa ggtgaaaagc   1260
cgccttctcc gagaactcga cgccctcgcc gcgatggctg agtcgcatcc gttcggcatt   1320
cccatgcggg atgacgattt catctggggc agcaacatgg tgctcttgaa ccgcgccatg   1380
gcgttcctgc tggccgaagg cgtcggtgtc cttcatcccg ctgcacatac ggtggcccag   1440
```

```
cgcgcggcgg actacctgtt tggcgcaaat ccgctcgggc agtgctacgt cacgggcttt    1500
ggccaacgcc ccgtgcgcca tccgcatcat cgcccgtccg tcgcggatga tgtggaccat    1560
cccgtccctg gcatggtcgt cggcggccca aaccgccacc tgcaggacga datcgcccgc    1620
gcacagcttg cggggagacc tgcgatggag gcgtacatcg atcaccagga cagctactcg    1680
accaacgagg tcgccgtcta ctggaattcg cctgccgtgt tgtcatcgc ggctttgctc    1740 gaggcgcgcg ggaggtgacg gatggctttc caggcaca                            1778

<210> SEQ ID NO 3
<211> LENGTH: 1029
<212> TYPE: DNA
<213> ORGANISM: Artificial Sequence
<220> FEATURE:
<223> OTHER INFORMATION: Synthetic sequence optimized for plant
      expression

<400> SEQUENCE: 3
ccacaagttt gtacaaaaaa gcaggctatg gggtcatccc accatcacca tcaccattcg      60
tctggtcttg tgccgagagg cagccatatg gctagtgcta tatacttaca tcatcagagc    120
ccgaatgtga aaacgagctc aatcacagtt acaacgaatg agactacaac cctcatgtca    180
ataacgacca acacagttcc aactacagtt actcccacca caagttctat accacaactc    240
atttatgtaa cttcatctgc ctcttcgccc accccagtct atttaaacaa tagcactgtc    300
ccaagcttct atttagaagt aaatatgtgg aatgcaaaaa cctggaacgg caattacact    360
atggttttta atccgctaac tcgtacttta agcgtctcct ttaacttaac acaagtcaat    420
cctcttcaat ggactaacgg ctatcctgaa atttacgtgg gcaggaagcc atgggacacg    480
tcatatgcag gcaatatttt ccccatgcgc attggtaata tgactccgtt catggtgtca    540
ttctacataa atctcacaaa attagatcct agcatcaatt ttgacattgc atcagatgca    600
tggatagtaa daccgcagat agctttcagt ccagggactg cgcctggaaa tggtgatatt    660
gaaataatgg tttggttgtt ctcacagaac ctacaaccag ctggccagca agtcggcgaa    720
gtagtcatac caatttacat aaatcatact ttagtcaacg ctacattcca ggtttggaag    780
atgaagaacg taccctgggg tggatgggag tacatcgctt tcaggcctga cggttggaaa    840
gtaactaatg gatatgtcgc gtatgagcca aacctattta aaaagccctt aaataacttc    900
gcatcttata acataacgaa ctactatcta actgattggg agtttggcac agaatgggga    960
actatgacat cgaatggtac agcttatttt agctggacta aagtaacctt ttacgaaaca    1020
ctactgtaa                                                           1029

<210> SEQ ID NO 4
<211> LENGTH: 1029
<212> TYPE: DNA
<213> ORGANISM: Artificial Sequence
<220> FEATURE:
<223> OTHER INFORMATION: Synthetic sequence optimized for expression in
      plants

<400> SEQUENCE: 4
ccacaagttt gtacaaaaaa gcaggctatg ggcagtagcc atcaccatca ccatcacagc      60 tctggggttag ttccccgcgg ttctcatatg gcgagcgcta tatatctaca tcatcaatcc    120
cctaatgtaa aaacaagctc cattactgtg acgactaatg aaaccacaac gttaatgtcg    180
ataactacga atactgtccc aacgacagtt accccccacca cttcatcgat acctcagctt    240
```

| | |
|---|---:|
| atatacgtaa catcttcagc atctagtcca actcccgtgt atctcaacaa ttcaactgtc | 300 |
| ccatcattct atctagaggt caatatgtgg aacgccaaaa catggaacgg caattacacg | 360 |
| atggtatttta atccattaac aagaactctc agcgtgtcat ttaatctgac tcaagtaaat | 420 |
| cctttacagt ggacaaatgg ataccctgaa atttacgttg gcaggaaacc atgggatact | 480 |
| agttatgcag gaaatatttt cccgatgaga ataggcaaca tgacaccgtt tatggtcagc | 540 |
| ttttatataa acttaacaaa actagatccg tcaattaact ttgatatagc atcggatgct | 600 |
| tggatagtca ggccacaaat tgcttttca ccagggacag ctcccggtaa cggcgacatc | 660 |
| gaaataatgg tctggttatt ctctcagaac ctacagccgg cgggtcagca agtcggtgaa | 720 |
| gttgtaatac caatatatat caaccatacc ttggttaacg ctaccttcca agtctggaaa | 780 |
| atgaagaatg taccttgggg aggttgggag tatatcgcat tccgtccgga cggctggaag | 840 |
| gttactaatg gctatgtggc ctacgagcca aacttattca ttaaggcact aaacaatttc | 900 |
| gcttcataca atattactaa ttattactta actgactggg aattcggaac tgaatggggc | 960 |
| actatgacaa gcaatggtac tgcttacttc agctggacaa taagtaactt ttatgagaca | 1020 |
| ctcctttaa | 1029 |

```
<210> SEQ ID NO 5
<211> LENGTH: 1637
<212> TYPE: DNA
<213> ORGANISM: Artificial Sequence
<220> FEATURE:
<223> OTHER INFORMATION: Synthetic sequence optimized for expression in
      plants

<400> SEQUENCE: 5
```

| | |
|---|---:|
| ggcgcgccgc caccatggca ccgtcccgtg ttcctaagtc tatctttat aaccaggtgg | 60 |
| ggtacctcat tagcggtgac aagaggttct ggattcaggc gcacgaaccg caaccgttcg | 120 |
| ctctccgtac tccggagggg caggccgttt tcgccggcat gactaaaccc gtcgaggta | 180 |
| actggtatgt cggagacttt accgcccttc gcgtgcctgg gacttatacc ctgacggtgg | 240 |
| gtaccctcga ggcgcgtgtt gtcatccacc ggagagctta tcgcgatgtc ttggaggcca | 300 |
| tgcttcgttt cttcgactac cagttgtgcg gggtcgtgct tccggaggac gaggcaggcc | 360 |
| cgtgggcaca cggtgcatgc catacttccg acgctaaagt gtttggtacg gagagggcat | 420 |
| ggcttgccc cggcggatgg catgatgcgg gagattacgg caagtataca gtgcctgctg | 480 |
| cgaaggctgt ggctgatctc ctccttgctc atgagtactt cccggccgcg ttggctcacg | 540 |
| tgcgccctat gcggtccgtg cacagggcgc cgcacctgcc tcccgctctg gaggtcgcga | 600 |
| gggaggaaat tgcttggctt ttgacgatgc aggatcccgc cactggggga gtttaccaca | 660 |
| aggtgaccac gccgtcattc ccgcctctgg acactcgccc agaggatgac gatgctccgc | 720 |
| tggtcctaag cccgatctcc tatgcagcaa cggctacatt ctgtgctgcc atggcgcatg | 780 |
| ctgcgctcgt ttatcgtccc ttcgatccgg ccctgtcctc atgttgcgcg gatgcggcca | 840 |
| ggagggcata cgcttggctc ggtgcgcacg agatgcagcc atttcacaac cccgacggga | 900 |
| ttctgacggg tgagtatggc gatgccgaac ttcgcgatga actgctatgg gctagctgtg | 960 |
| cgttgctcag gatgacgggc gattctgcgt gggctagagt ttgcgaacct ctcctggatc | 1020 |
| ttgatttgcc ctgggaactc gggtgggcag atgttgctct gtacggtgtt atggattatc | 1080 |
| tgcgcacccc cagggctgcc gttagtgacg atgttaggaa caaggtcaag tcccgccttc | 1140 |
| tgagagaact tgatgccttg gccgccatgg cagaatccca tccatttggt ataccctatgc | 1200 |

```
gggacgatga cttcatctgg ggctctaata tggtcctttt gaaccgggcc atggctttcc    1260
tcctggcaga gggcgttggc gtgttgcacc ctgctgccca tactgtcgcc cagagagctg    1320
ccgactatct gttcggcgca aaccccctgg gtcaatgcta cgtgacaggc ttcgggcaga    1380
ggccggttag gcacccgcat catcggccga gcgtcgcaga tgacgtggac catccggtgc    1440
ctgggatggt ggtgggggc cccaacaggc atcttcaaga cgaaattgcg cgcgcacagc     1500
tagctggccg cccagccatg gaagcctaca tcgatcatca ggatagctac tctaccaatg    1560
aggttgccgt ttattggaac tcgcccgcgg tcttcgtgat agcggcactt ttggaggccc    1620
gcggtcgctg aactagt                                                   1637
```

```
<210> SEQ ID NO 6
<211> LENGTH: 77
<212> TYPE: DNA
<213> ORGANISM: Artificial Sequence
<220> FEATURE:
<223> OTHER INFORMATION: Synthetic apoplast targeting sequence

<400> SEQUENCE: 6
gctactacta agcatttggc tcttgccatc cttgtcctcc ttagcattgg tatgaccacc     60
agtgcaagaa ccctcct                                                    77

<210> SEQ ID NO 7
<211> LENGTH: 31
<212> TYPE: DNA
<213> ORGANISM: Artificial Sequence
<220> FEATURE:
<223> OTHER INFORMATION: Primer/probe sequence

<400> SEQUENCE: 7
cgtcaagacc agtagtatta ccgttacaac g                                    31

<210> SEQ ID NO 8
<211> LENGTH: 23
<212> TYPE: DNA
<213> ORGANISM: Artificial Sequence
<220> FEATURE:
<223> OTHER INFORMATION: Primer/probe sequence

<400> SEQUENCE: 8
cacgtagccg ttcgtaacct tcc                                             23

<210> SEQ ID NO 9
<211> LENGTH: 20
<212> TYPE: DNA
<213> ORGANISM: Artificial Sequence
<220> FEATURE:
<223> OTHER INFORMATION: Primer/probe sequence

<400> SEQUENCE: 9
cgtcccgtgt tcctaagtct                                                 20

<210> SEQ ID NO 10
<211> LENGTH: 20
<212> TYPE: DNA
<213> ORGANISM: Artificial Sequence
<220> FEATURE:
<223> OTHER INFORMATION: Primer/probe sequence

<400> SEQUENCE: 10
aacggcaacc tcattggtag                                                 20
```

```
<210> SEQ ID NO 11
<211> LENGTH: 20
<212> TYPE: DNA
<213> ORGANISM: Artificial Sequence
<220> FEATURE:
<223> OTHER INFORMATION: Primer/probe sequence

<400> SEQUENCE: 11
cgttacaacg aacgagacca                                              20

<210> SEQ ID NO 12
<211> LENGTH: 20
<212> TYPE: DNA
<213> ORGANISM: Artificial Sequence
<220> FEATURE:
<223> OTHER INFORMATION: Primer/probe sequence

<400> SEQUENCE: 12
cacgtagccg ttcgtaacct                                              20

<210> SEQ ID NO 13
<211> LENGTH: 312
<212> TYPE: PRT
<213> ORGANISM: Artificial Sequence
<220> FEATURE:
<223> OTHER INFORMATION: Synthetic bacterial peptide sequence expressed
      in plants

<400> SEQUENCE: 13

Met Ala Ile Tyr Leu His His Gln Ser Pro Asn Val Lys Thr Ser Ser
1               5                   10                  15

Ile Thr Val Thr Thr Asn Glu Thr Thr Thr Leu Met Ser Ile Thr Thr
            20                  25                  30

Asn Thr Val Pro Thr Thr Val Thr Pro Thr Thr Ser Ser Ile Pro Gln
        35                  40                  45

Leu Ile Tyr Val Thr Ser Ser Ala Ser Ser Pro Thr Pro Val Tyr Leu
    50                  55                  60

Asn Asn Ser Thr Val Pro Ser Phe Tyr Leu Glu Val Asn Met Trp Asn
65                  70                  75                  80

Ala Lys Thr Trp Asn Gly Asn Tyr Thr Met Val Phe Asn Pro Leu Thr
                85                  90                  95

Arg Thr Leu Ser Val Ser Phe Asn Leu Thr Gln Val Asn Pro Leu Gln
            100                 105                 110

Trp Thr Asn Gly Tyr Pro Glu Ile Tyr Val Gly Arg Lys Pro Trp Asp
        115                 120                 125

Thr Ser Tyr Ala Gly Asn Ile Phe Pro Met Arg Ile Gly Asn Met Thr
    130                 135                 140

Pro Phe Met Val Ser Phe Tyr Ile Asn Leu Thr Lys Leu Asp Pro Ser
145                 150                 155                 160

Ile Asn Phe Asp Ile Ala Ser Asp Ala Trp Ile Val Arg Pro Gln Ile
                165                 170                 175

Ala Phe Ser Pro Gly Thr Ala Pro Gly Asn Gly Asp Ile Glu Ile Met
            180                 185                 190

Val Trp Leu Phe Ser Gln Asn Leu Gln Pro Ala Gly Gln Gln Val Gly
        195                 200                 205

Glu Val Val Ile Pro Ile Tyr Ile Asn His Thr Leu Val Asn Ala Thr
    210                 215                 220

Phe Gln Val Trp Lys Met Lys Asn Val Pro Trp Gly Gly Trp Glu Tyr
225                 230                 235                 240
```

```
Ile Ala Phe Arg Pro Asp Gly Trp Lys Val Thr Asn Gly Tyr Val Ala
                245                 250                 255

Tyr Glu Pro Asn Leu Phe Ile Lys Ala Leu Asn Asn Phe Ala Ser Tyr
            260                 265                 270

Asn Ile Thr Asn Tyr Tyr Leu Thr Asp Trp Glu Phe Gly Thr Glu Trp
        275                 280                 285

Gly Thr Met Thr Ser Asn Gly Thr Ala Tyr Phe Ser Trp Thr Ile Ser
    290                 295                 300

Asn Phe Tyr Glu Thr Leu Leu Glx
305                 310

<210> SEQ ID NO 14
<211> LENGTH: 539
<212> TYPE: PRT
<213> ORGANISM: Artificial Sequence
<220> FEATURE:
<223> OTHER INFORMATION: Synthetic bacterial peptide sequence expressed
      in plants

<400> SEQUENCE: 14

Met Ala Pro Ser Arg Val Pro Lys Ser Ile Phe Tyr Asn Gln Val Gly
1               5                   10                  15

Tyr Leu Ile Ser Gly Asp Lys Arg Phe Trp Ile Gln Ala His Glu Pro
            20                  25                  30

Gln Pro Phe Ala Leu Arg Thr Pro Glu Gly Gln Ala Val Phe Ala Gly
        35                  40                  45

Met Thr Lys Pro Val Gly Gly Asn Trp Tyr Val Gly Asp Phe Thr Ala
    50                  55                  60

Leu Arg Val Pro Gly Thr Tyr Thr Leu Thr Val Gly Thr Leu Glu Ala
65                  70                  75                  80

Arg Val Val Ile His Arg Ala Tyr Arg Asp Val Leu Glu Ala Met
                85                  90                  95

Leu Arg Phe Phe Asp Tyr Gln Leu Cys Gly Val Val Leu Pro Glu Asp
            100                 105                 110

Glu Ala Gly Pro Trp Ala His Gly Ala Cys His Thr Ser Asp Ala Lys
        115                 120                 125

Val Phe Gly Thr Glu Arg Ala Leu Ala Cys Pro Gly Gly Trp His Asp
    130                 135                 140

Ala Gly Asp Tyr Gly Lys Tyr Thr Val Pro Ala Ala Lys Ala Val Ala
145                 150                 155                 160

Asp Leu Leu Leu Ala His Glu Tyr Phe Pro Ala Ala Leu Ala His Val
                165                 170                 175

Arg Pro Met Arg Ser Val His Arg Ala Pro His Leu Pro Pro Ala Leu
            180                 185                 190

Glu Val Ala Arg Glu Glu Ile Ala Trp Leu Leu Thr Met Gln Asp Pro
        195                 200                 205

Ala Thr Gly Gly Val Tyr His Lys Val Thr Thr Pro Ser Phe Pro Pro
    210                 215                 220

Leu Asp Thr Arg Pro Glu Asp Asp Ala Pro Leu Val Leu Ser Pro
225                 230                 235                 240

Ile Ser Tyr Ala Ala Thr Ala Thr Phe Cys Ala Ala Met Ala His Ala
                245                 250                 255

Ala Leu Val Tyr Arg Pro Phe Asp Pro Ala Leu Ser Ser Cys Cys Ala
            260                 265                 270

Asp Ala Ala Arg Arg Ala Tyr Ala Trp Leu Gly Ala His Glu Met Gln
        275                 280                 285
```

-continued

```
Pro Phe His Asn Pro Asp Gly Ile Leu Thr Gly Glu Tyr Gly Asp Ala
    290                 295                 300

Glu Leu Arg Asp Glu Leu Leu Trp Ala Ser Cys Ala Leu Leu Arg Met
305                 310                 315                 320

Thr Gly Asp Ser Ala Trp Ala Arg Val Cys Glu Pro Leu Leu Asp Leu
                325                 330                 335

Asp Leu Pro Trp Glu Leu Gly Trp Ala Asp Val Ala Leu Tyr Gly Val
            340                 345                 350

Met Asp Tyr Leu Arg Thr Pro Arg Ala Ala Val Ser Asp Asp Val Arg
            355                 360                 365

Asn Lys Val Lys Ser Arg Leu Leu Arg Glu Leu Asp Ala Leu Ala Ala
    370                 375                 380

Met Ala Glu Ser His Pro Phe Gly Ile Pro Met Arg Asp Asp Asp Phe
385                 390                 395                 400

Ile Trp Gly Ser Asn Met Val Leu Leu Asn Arg Ala Met Ala Phe Leu
                405                 410                 415

Leu Ala Glu Gly Val Gly Val Leu His Pro Ala Ala His Thr Val Ala
            420                 425                 430

Gln Arg Ala Ala Asp Tyr Leu Phe Gly Ala Asn Pro Leu Gly Gln Cys
            435                 440                 445

Tyr Val Thr Gly Phe Gly Gln Arg Pro Val Arg His Pro His His Arg
    450                 455                 460

Pro Ser Val Ala Asp Asp Val Asp His Pro Val Pro Gly Met Val Val
465                 470                 475                 480

Gly Gly Pro Asn Arg His Leu Gln Asp Glu Ile Ala Arg Ala Gln Leu
                485                 490                 495

Ala Gly Arg Pro Ala Met Glu Ala Tyr Ile Asp His Gln Asp Ser Tyr
            500                 505                 510

Ser Thr Asn Glu Val Ala Val Tyr Trp Asn Ser Pro Ala Val Phe Val
    515                 520                 525

Ile Ala Ala Leu Leu Glu Ala Arg Gly Arg Glx
    530                 535
```